(12) United States Patent
Krasnoperov

(10) Patent No.: US 12,673,090 B2
(45) Date of Patent: Jul. 7, 2026

(54) TREATMENT OF CANCERS USING SEPHB4-HSA FUSION PROTEINS

(71) Applicant: Vasgene Therapeutics Inc, Los Angeles, CA (US)

(72) Inventor: Valery Krasnoperov, Pasadena, CA (US)

(73) Assignee: Vasgene Therapeutics Inc, Los Angeles, CA (US)

( * ) Notice: Subject to any disclaimer, the term of this patent is extended or adjusted under 35 U.S.C. 154(b) by 1192 days.

(21) Appl. No.: 17/439,926

(22) PCT Filed: Mar. 17, 2020

(86) PCT No.: PCT/US2020/023215
§ 371 (c)(1),
(2) Date: Sep. 16, 2021

(87) PCT Pub. No.: WO2020/190977
PCT Pub. Date: Sep. 24, 2020

(65) Prior Publication Data
US 2022/0249621 A1 Aug. 11, 2022

Related U.S. Application Data

(60) Provisional application No. 62/819,725, filed on Mar. 18, 2019, provisional application No. 62/819,642, filed on Mar. 17, 2019.

(51) Int. Cl.
*A61K 38/38* (2006.01)
*A61K 38/17* (2006.01)
(Continued)

(52) U.S. Cl.
CPC .......... *A61K 38/385* (2013.01); *A61K 38/179* (2013.01); *A61K 39/3955* (2013.01); *A61K 45/06* (2013.01); *A61P 35/00* (2018.01)

(58) Field of Classification Search
None
See application file for complete search history.

(56) References Cited

U.S. PATENT DOCUMENTS 8,063,183 B2 11/2011 Krasnoperov et al.
9,533,026 B2 1/2017 Krasnoperov et al.
(Continued)

FOREIGN PATENT DOCUMENTS

WO 2002026827 A2 4/2002
WO 2008112290 9/2008
(Continued)

OTHER PUBLICATIONS

Kumar et al., "Crk adaptor protein promotes PD-L 1 expression, EMT and immune evasion in a murine model of triple-negative breast cancer", OncoImmunology, 2018, vol. 7, No. 1, Sep. 27, 2017 (Sep. 27, 2017).

(Continued)

*Primary Examiner* — Aurora M Fontainhas
*Assistant Examiner* — Selam Berhane
(74) *Attorney, Agent, or Firm* — Craig A Crandall, APC; Craig A Crandall

(57) ABSTRACT

Compositions and methods are provided for treating cancer in a subject comprising administering to the subject a therapeutically effective amount of a polypeptide agent that inhibits EphB4 or EphrinB2 mediated functions. In various embodiments the methods further provide administration of a therapeutically effective amount of an immune checkpoint inhibitor. The present inventors have demonstrated that the synergistic effect of the combination of an EphB4-EphrinB2 inhibitor and checkpoint inhibitor provides superior progression-free survival (PFS) and objective response rates (ORR) patients with various cancers by activating T cell and promoting T cell and NK cell trafficking into the tumor and (Continued)

via migration of immune cells (e.g., CD3 and CD8) into the tumor.

8 Claims, 14 Drawing Sheets
(11 of 14 Drawing Sheet(s) Filed in Color)

Specification includes a Sequence Listing.

(51) Int. Cl.

| | | |
|---|---|---|
| *A61K 39/395* | (2006.01) | |
| *A61K 45/06* | (2006.01) | |
| *A61P 35/00* | (2006.01) | |

(56) References Cited

U.S. PATENT DOCUMENTS

| | | |
|---|---|---|
| 2005/0249736 A1 | 11/2005 | Krasnoperov et al. |
| 2006/0039904 A1 | 2/2006 | Wu et al. |
| 2010/0261653 A1 | 10/2010 | Krasnoperov et al. |

FOREIGN PATENT DOCUMENTS

| | | |
|---|---|---|
| WO | 2020168110 A1 | 8/2020 |
| WO | 2020190977 | 9/2020 |

OTHER PUBLICATIONS

Li et al., "EphB4-EphrinB2 receptor-ligand are downstream effectors and novel targets of PTEN deficient prostate cancer", Cancer Research, American Association for Cancer Research, Jul. 1, 2019 (Jul. 1, 2019).

PCT International Search Report, Jul. 16, 2020.

Alessio et al., "Targeting Eph/ephrin system in cancer therapy", European Journal of Medicinal Chemistry, vol. 142, pp. 152-162, Jul. 29, 2017.

Liu et al "EphB4 as a therapeutic target in mesothelioma", BMC Cancer, vol. 13, No. p. 269, May 30, 2013.

Bhatia et al "Inhibition of EphB4-Ephrin-B2 Signalling Reprograms the Tumor Immune Microenvironment in Head and Neck Cancers", Cancer Research, vol. 79, No. 10, pp. 2722-2735, May 15, 2019.

Anonymous, "History of Changes for Study: NCT02717156, Combination Therapy With Pembrolizumab and sEphB4-HSA in Previously Treated Urothelial Carcino", Retrieved from the Internet, pp. 1-6, May 17, 2018.

Anonymous, "History of Changes for Study; NCT03049618, Recombinant EphB4-HSA Fusion Protein and Pembrolizumab, MK-3475", Retrieved from the Internet, pp. 1-6, Mar. 30, 2018.

PD-L1/DAPI

FIGS. 11A-B

TREATMENT OF CANCERS USING SEPHB4-HSA FUSION PROTEINS

RELATED PATENT APPLICATIONS

This application claims benefit of U.S. Provisional Application No. 62/819,642, filed on Mar. 17, 2019 and U.S. Provisional Application No. 62/819,725, filed on Mar. 18, 2019, each incorporated in its entirety by reference herein.

SEQUENCE LISTING

The instant application contains a Sequence Listing in the form of a "paper copy" (PDF File) and a file containing the referenced sequences (SEQ ID NOS: 1-2) in computer readable form (ST25 format text file) which is submitted herein. The Sequence Listing is shown using standard three letter code for amino acids, as defined in 37 C.F.R. 1.822.

TECHNICAL FIELD

Today, cancer remains a major cause of death worldwide despite the numerous advanced diagnostic and therapeutic methods that have been developed. Curative treatment protocols in clinical oncology remain reliant upon a combination of surgical resection, ionizing radiation, and cytotoxic chemotherapy. The major barrier to successful treatment and prevention of cancer lies in the fact that many cancers still fail to respond to the current chemotherapeutic and immunotherapy intervention, and many individuals suffer a recurrence or death, even after aggressive therapy. To address these shortcomings, there has been a trend in drug discovery to develop targeted therapies capable of modulating signaling axes dysregulated in cancers. There are now many FDA approved antibodies and small molecules that allow for therapeutic manipulation of a myriad of clinically relevant targets.

Cancer immunotherapy is the name given to cancer treatments that use the immune system to attack cancers. Systemic immunotherapy refers to immunotherapy that is used to treat the whole body and is more commonly used than local immunotherapy which is used to treat one "localized" part of the body, particularly when a cancer has spread. Although cancer cells are less immunogenic than pathogens, the immune system is clearly capable of recognizing and eliminating tumor cells, and cancer immunotherapy attempts to harness the exquisite power and specificity of the immune system for treatment of malignancy. Unfortunately, tumors frequently interfere with the development and function of immune responses, e.g., the suppressive milieu present within established tumors inhibits effective immune responses. The goal of immunotherapy is ultimately to re-establish immune system antitumor vigilance and to inhibit tumor and tumor-microenvironment immunosuppression. Thus, the challenge for immunotherapy is to use advances in cellular and molecular immunology to develop strategies which manipulates the local tumor environment to promote a pro-inflammatory environment, to promote dendritic cell activation, and to effectively and safely augment anti-tumor responses.

Immunotherapy using agonistic, antagonistic, or blocking antibodies to co-stimulatory or co-inhibitory molecules (immune checkpoints) has been an area of extensive research and clinical evaluation. Immune checkpoint proteins include CTLA-4, PD-1, PD-L1, LAG-3, and TIM-3 as well as several others (Sharpe et al., Nat Immunol, 8:239-45, 2007). Under normal physiological conditions, immune checkpoints are crucial for the maintenance of self-tolerance (that is, the prevention of autoimmunity) and protect tissues from damage when the immune system is responding to pathogenic infection. It is now also clear that tumors co-opt certain immune-checkpoint pathways as a major mechanism of immune resistance, particularly against T cells that are specific for tumor antigens (Pardoll D M., Nat Rev Cancer, 12:252-64, 2012). Accordingly, treatment utilizing antibodies to immune checkpoint molecules including, e.g., CTLA-4 (ipilimumab), PD-1 (nivolumab; pembrolizumab; pidilizumab) and PD-L1 (BMS-936559; MPLD3280A; MED14736; MSB0010718C)(see, e.g, Philips and Atkins, International Immunology, 27(1); 39-46, October 2014), and OX-40, CD137, GITR, LAGS, TIM-3, and VISTA (see, e.g., Sharon et al., Chin J Cancer., 33(9): 434-444, September 2014; Hodi et al., N Engl J Med, 2010; Topalian et al., N Engl J Med, 366:2443-54) are being evaluated as new, alternative immunotherapies to treat patients with proliferative diseases such as cancer, and in particular, patients with refractory and/or recurrent cancers.

CTLA-4 antibodies were the first of this class of "checkpoint inhibitor" immunotherapeutics to achieve US Food and Drug Administration (FDA) approval. Clinical development of anti-CTLA-4 antibodies, including ipilimumab and tremelimumab, as novel therapeutic strategies to augment anti-tumor immunity in cancer is ongoing. Both ipilimumab and tremelimumab have been evaluated extensively in melanoma; notably, ipilimumab was recently approved as monotherapy for the treatment of advanced melanoma. Tremelimumab is currently undergoing evaluation in phase II trials as monotherapy in melanoma and malignant mesothelioma, while ipilimumab is under clinical investigation in phase II and III trials in various tumor types, including in melanoma, prostate, and lung cancers as monotherapy and with other therapeutic modalities, such as chemotherapy and radiation (Grosso et al., Cancer Immunity, Vol. 13, pg 5, 22 Jan. 2013).

Inhibition of the PD-1/PD-L1 interaction mediates potent antitumor activity in preclinical models (U.S. Pat. Nos. 8,008,449 and 7,943,743), and the use of Ab inhibitors of the PD-1/PD-L1 interaction for treating cancer has entered clinical trials (see, e.g., Topalian et al., Curr Opin Immunol., 24:207-212, 2012; Brahmer et al., N Engl J Med., 366(26): 2455-65, 2012; Garon et al., N Engl J Med, 372:2018-2028, 2015; Philips et al., Int. Immunol., 27(1): 39-46, 2015). PD-L1 expression has been found in several murine and human cancers, including human lung, ovarian and colon carcinoma and various myelomas, and anti-PD-L1 antibodies developed by, e.g., Brsitol-Myers Squibb (BMS-936559), Medimmune (MED14736), Genentech (MPDL3280A), Merck/Pfizer (MSB0010718C) have been, or are currently being, clinically evaluated.

Currently, checkpoint inhibitor therapy has become the preferred second- or third-line therapy for many cancers, and PD1/PDL1 antibodies have changed the treatment paradigm for several cancers. Despite these significant advancements, there remains a major need to improve on the current state-of-the-art. For example, checkpoint inhibitor therapy remains limited by concerns over potential severe side effects and the fact that many tumors lack the targeted antigen and will therefore evade treatment. In general, about 20% of patients with various cancers respond to PD-1/PD-L1 antibodies or CTLA-4 antibodies and overall survival remains less than a year in most instances and objective response rates are modest, underscoring the large unmet need for nearly 70-80% of these patients.

Innovative trials of chemo-immunotherapy combinations in the frontline setting are ongoing. The results from the first of such trials combining atezolizumab+platinum-based chemotherapy was presented at ESMO on Sep. 30, 2019 missing the co-primary endpoint of OS and meeting the PFS endpoint. Notably, the ORR was 49% (44% for chemotherapy alone), PFS was 8.2 months (6.3 for chemotherapy alone), and OS was 16 months (13.4 months for chemo alone). These data indicate that the standard of care has not changed, and that there does not appear to be a synergy between chemo and immunotherapy in this setting and with no predictive value for the biomarker, i.e., PD-L1 expression.

Concerted efforts to understand the factors involved in resistance to immunotherapy within the tumor microenvironment (TME) have led to the identification of T regulatory cells (Tregs) and tumor-associated macrophages (TAMs) as key regulators of tumor growth and therapeutic response (Messenheimer D J, et al., Clin Cancer Res, 23:6165-77, 2017). Studies have shown a correlation between high Treg/TAM infiltrates and poor survival outcomes (Pitt J M, et al., Ann Oncol, 27:1482-92, 2016) and/or poor response to chemotherapeutic agents. Targeted depletion of Tregs or TAMs has been reported to improve the response to chemotherapy and checkpoint inhibitors in different tumor models (Arce Vargas F, et al., Immunity, 46:577-86, 2017). However, data from clinical trials suggest lack of efficacy following treatment with Treg-targeted immunotherapies such as anti-CTLA-4 (Robert C, Schachter et al., N Engl J Med, 372:2521-32, 2015). Therefore, there is an unmet need for alternate approaches that can both target immunosuppressive cell populations within the TME and enhance therapeutic benefit.

INCORPORATION BY REFERENCE

Patent documents U.S. Pat. Nos. 7,381,410; 7,862,816; 7,977,463; 8,063,183; 8,273,858; 8,975,377; 8,981,062; 9,533,026; and all references disclosed herein are hereby incorporated by reference in their entirety for all purposes.

DISCLOSURE OF THE INVENTION

As described herein, the present inventors have built upon the success of PD1/PD-L1 targeted therapy by addressing the tumors with a few or no immune cells (cold tumors) and that are unlikely to respond to immunotherapy, by evaluating agents that recruit immune cells to the tumors. Specifically, EphrinB2 and its high affinity cognate receptor-EphB4 are transmembrane proteins that are induced in tumor vessels and regulate immune cell trafficking. Soluble extracellular fragment of EphB4 fused to albumin (sEphB4-HSA) blocks interaction between EphrinB2 and EphB4, and blocks bidirectional signaling, thus promoting immune cell trafficking. The present inventors have determined that inhibition of EphB4-EphrinB2 interaction can induce an anti-tumor immune response in various cancers. The present inventors have evaluated the efficacy of sEphB4-HSA, alone and in combination with a PD-1/PD-L1 targeting antibody and a CTLA-4 targeting antibody, as front-line treatment of various cancers, or alternatively for the treatment of patients whose disease has progressed after receiving at least one line of platinum-based chemotherapy, radiation therapy, or checkpoint inhibitor therapy. The present inventors have demonstrated that the synergistic effect of the combination provides superior progression-free survival (PFS) and objective response rates (ORR) patients with various cancers by activating T cell and promoting T cell and NK cell trafficking into the tumor and via migration of immune cells (e.g., CD3 and CD8) into the tumor.

In one aspect, the present invention relates to use of a polypeptide agent that inhibits EphB4 or EphrinB2 mediated functions in preparing a medicament for use, alone or in combination with an immune checkpoint inhibitor, in treating a cancer. In various embodiments, the cancer is selected from the group consisting of, but not limited to, non-small cell lung carcinoma (NSCLC), colon carcinoma, metastatic urothelial cancer, breast cancer, renal cell carcinoma (RCC), hepatocellular carcinoma (HCC), mesothelioma, pancreatic cancer, prostate cancer, bladder cancer, squamous cell carcinoma of the head and neck (HNSCC), Kaposi sarcoma, and leukemia. In various embodiments, the cancer tumors express EphrinB2. In various embodiments, the cancer tumors express PD-L1. In various embodiments, the cancer tumors express EphrinB2 and PD-L1.

In various embodiments, the polypeptide agent that inhibits EphB4 or EphrinB2 mediated functions is a monomeric ligand binding portion of the EphB4 protein or EphrinB2 protein, or an antibody that binds to and affects EphB4 or EphrinB2. In various embodiments, the polypeptide agent is a soluble EphB4 (sEphB4) polypeptide that binds specifically to an EphrinB2 polypeptide and comprises an amino acid sequence of an extracellular domain of an EphB4 protein. In various embodiments, the sEphB4 polypeptide comprises a globular domain of an EphB4 protein.

In various embodiments, the sEphB4 polypeptide comprises a sequence selected from the group consisting of a sequence that is at least 90% identical to residues 1-522, at least 90% identical to residues 1-412, and at least 90% identical to residues 1-312 of the amino acid sequence of SEQ ID NO: 1. In various embodiments, the sEphB4 polypeptide may comprise a sequence encompassing the globular (G) domain (amino acids 29-197 of SEQ ID NO; 1), and optionally additional domains, such as the cysteine-rich domain (amino acids 239-321 of SEQ ID NO: 1), the first fibronectin type 3 domain (amino acids 324-429 of SEQ ID NO: 1) and the second fibronectin type 3 domain (amino acids 434-526 of SEQ ID NO: 1). In various embodiments, the sEphB4 polypeptide will comprise amino acids 1-537 of SEQ ID NO: 1. In various embodiments, the sEphB4 polypeptide will comprise amino acids 1-427 of SEQ ID NO: 1. In various embodiments, the sEphB4 polypeptide will comprise amino acids 1-326 of SEQ ID NO: 1. In various embodiments, the sEphB4 polypeptide will comprise amino acids 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537 of SEQ ID NO: 1. In various embodiments, the sEphB4 polypeptide will comprise amino acids 16-197, 16-312, 16-321, 16-326, 16-412, 16-427, 16-429, 16-526, and 16-537 of SEQ ID NO: 1.

In various embodiments, a soluble polypeptide may be prepared in a multimeric form, by, for example, expressing as an Fc fusion protein or fusion with another multimerization domain.

In various embodiments, the sEphB4 polypeptide will further comprise an additional component that confers increased serum half-life while still retaining EphrinB2 binding activity. In various embodiments, the sEphB4 polypeptides are monomeric and are covalently linked to one or more polyoxyaklylene groups (e.g., polyethylene, polypropylene). In various embodiments, the sEphB4 polypeptide is covalently linked to a polyethylene glycol (PEG) group(s) (hereinafter "sEphB4-PEG").

In various embodiments, the sEphB4 polypeptide is stably associated with a second stabilizing polypeptide that confers improved half-life without substantially diminishing EphrinB2 binding. In various embodiments, the stabilizing polypeptide is immunocompatible with human patients (or animal patients, where veterinary uses are contemplated) and will have little or no significant biological activity. In various embodiments, the sEphB4 polypeptide is associated covalently or non-covalently with an albumin selected from the group consisting of a human serum albumin (HSA) (hereinafter "sEphB4-HSA") and bovine serum albumin (BSA) (hereinafter "sEphB4-BSA"). In various embodiments, the sEphB4-HSA comprises residues 16-197 of SEQ ID NO: 1 directly fused to residues 25-609 of SEQ ID NO: 2. In various embodiments, the sEphB4-HSA comprises residues 16-312 of SEQ ID NO: 1 directly fused to residues 25-609 of SEQ ID NO: 2. In various embodiments, the sEphB4-HSA comprises residues 16-321 of SEQ ID NO: 1 directly fused to residues 25-609 of SEQ ID NO: 2. In various embodiments, the sEphB4-HSA comprises residues 16-326 of SEQ ID NO: 1 directly fused to residues 25-609 of SEQ ID NO: 2. In various embodiments, the sEphB4-HSA comprises residues 16-412 of SEQ ID NO: 1 directly fused to residues 25-609 of SEQ ID NO: 2. In various embodiments, the sEphB4-HSA comprises residues 16-427 of SEQ ID NO: 1 directly fused to residues 25-609 of SEQ ID NO: 2. In various embodiments, the sEphB4-HSA comprises residues 16-429 of SEQ ID NO: 1 directly fused to residues 25-609 of SEQ ID NO: 2. In various embodiments, the sEphB4-HSA comprises residues 16-526 of SEQ ID NO: 1 directly fused to residues 25-609 of SEQ ID NO: 2. In various embodiments, the sEphB4-HSA comprises residues 16-537 of SEQ ID NO: 1 directly fused to residues 25-609 of SEQ ID NO: 2.

In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancer is refractory to platinum-based chemotherapy. In various embodiments, the cancer is refractory to immunotherapy treatment. In various embodiments, the cancer is refractory to treatment with a chemotherapeutic agent. In various embodiments, the cancer is refractory to treatment using depleting antibodies to specific tumor antigens. In various embodiments, the cancer is refractory to treatment using agonistic, antagonistic, or blocking antibodies to co-stimulatory or co-inhibitory molecules (immune checkpoints). In various embodiments, the cancer is refractory to targeted treatment with an immunoconjugate, antibody-drug conjugate (ADC), or fusion molecule comprising a depleting antibody to specific tumor antigens tumor antigen and a cytotoxic agent. In various embodiments, the cancer is refractory to targeted treatment with a small molecule kinase inhibitor. In various embodiments, the cancer is refractory to treatment using surgery. In various embodiments, the cancer is refractory to treatment using stem cell transplantation. In various embodiments, the cancer is refractory to treatment using radiation. In various embodiments, the cancer is refractory to combination therapy involving, for example, two or more of: immunotherapy treatment, treatment with a platinum based chemotherapeutic agent, treatment with a tumor antigen-specific, depleting antibody, treatment with a immunoconjugate, ADC, or fusion molecule comprising a tumor antigen-specific, depleting antibody and a cytotoxic agent, targeted treatment with a small molecule kinase inhibitor, treatment using surgery, treatment using stem cell transplantation, and treatment using radiation.

In another aspect, the present invention relates to the use of a polypeptide agent that inhibits EphB4 or EphrinB2 mediated functions in preparing a medicament for use in a combination therapy for treating a cancer in a subject. In various embodiments, the combination therapy has a synergistic effect for the treatment of cancer.

In various embodiments, the use relates to methods of treating metastatic urothelial carcinoma in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the cancer is a relapsed/refractory cisplatin failed or intolerant urothelial cancer. In various embodiments, the urothelial carcinoma is refractory to treatment using platinum-based chemotherapy and/or radiation therapy. In various embodiments, the urothelial carcinoma is refractory to treatment using a checkpoint inhibitor. In various embodiments, the subject has relapsed urothelial carcinoma.

In various embodiments, the use relates to methods of treating non-small cell lung carcinoma (NSCLC) in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the NSCLC is refractory to treatment using platinum-based chemotherapy and/or radiation therapy. In various embodiments, the NSCLC is refractory to treatment using a checkpoint inhibitor. In various embodiments, the subject has relapsed NSCLC.

In various embodiments, the use relates to methods of treating hepatocellular carcinoma (HCC) in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the HCC is refractory to treatment using platinum-based chemotherapy and/or radiation therapy. In various embodiments, the HCC is refractory to treatment using a checkpoint inhibitor. In various embodiments, the subject has relapsed HCC.

In various embodiments, the use relates to methods of treating colon carcinoma in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the colon carcinoma is refractory to treatment using platinum-based chemotherapy and/or radiation therapy. In various embodiments, the colon carcinoma is refractory to treatment using a checkpoint inhibitor. In various embodiments, the subject has relapsed colon carcinoma.

In various embodiments, the use relates to methods of treating renal cell carcinoma (RCC) in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the RCC is refractory to treatment using platinum-based chemotherapy and/or radiation therapy. In various embodiments, the RCC is refractory to treatment using a checkpoint inhibitor. In various embodiments, the subject has relapsed RCC.

In various embodiments, the use relates to methods of treating squamous cell carcinoma of the head and neck (HNSCC) in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the HNSCC is refractory to treatment using platinum-based chemotherapy and/or radiation therapy. In various embodiments, the HNSCC is refractory to treatment using a checkpoint inhibitor. In various embodiments, the subject has relapsed HNSCC.

In various embodiments, the use relates to methods of treating Kaposi sarcoma (KS) in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the KS is refractory to treatment using platinum-based chemotherapy and/or radiation therapy. In various embodiments, the KS is refractory to treatment using a checkpoint inhibitor. In various embodiments, the subject has relapsed KS.

In various embodiments, the use relates to methods of treating breast cancer in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the breast cancer is refractory to treatment using platinum-based chemotherapy and/or radiation therapy. In various embodiments, the breast cancer is refractory to treatment using a checkpoint inhibitor. In various embodiments, the subject has relapsed breast cancer.

In various embodiments, the use relates to methods of treating mesothelioma in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the mesothelioma is refractory to treatment using platinum-based chemotherapy and/or radiation therapy. In various embodiments, the mesothelioma is refractory to treatment using a checkpoint inhibitor. In various embodiments, the subject has relapsed mesothelioma.

In various embodiments, the use relates to methods of treating prostate cancer in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the prostate cancer is refractory to treatment using platinum-based chemotherapy and/or radiation therapy. In various embodiments, the prostate cancer is refractory to treatment using a checkpoint inhibitor. In various embodiments, the subject has relapsed prostate cancer.

In various embodiments, the use relates to methods of treating pancreatic cancer in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the pancreatic cancer is refractory to treatment using platinum-based chemotherapy and/or radiation therapy. In various embodiments, the pancreatic cancer is refractory to treatment using a checkpoint inhibitor. In various embodiments, the subject has relapsed pancreatic cancer.

In various embodiments, the use relates to methods of treating bladder cancer in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the bladder cancer is refractory to treatment using platinum-based chemotherapy and/or radiation therapy. In various embodiments, the bladder cancer is refractory to treatment using a checkpoint inhibitor. In various embodiments, the subject has relapsed bladder cancer.

In various embodiments, the use relates to methods of treating leukemia in a subject, comprising administering to the subject a) a therapeutically effective amount of an sEphB4-HSA polypeptide, and b) a therapeutically effective amount of a checkpoint inhibitor. In various embodiments, the checkpoint inhibitor is a PD-1 inhibitor. In various embodiments, the leukemia is refractory to treatment using platinum-based chemotherapy and/or radiation therapy. In various embodiments, the leukemia is refractory to treatment using a checkpoint inhibitor. In various embodiments, the subject has relapsed leukemia.

In various embodiments, the methods comprise one or more additional anti-cancer therapies selected from the group consisting of immunotherapy, chemotherapy, targeted treatment using depleting antibodies to specific tumor antigens, targeted treatment using agonistic, antagonistic, or blocking antibodies to co-stimulatory or co-inhibitory molecules (immune checkpoints), targeted treatment with an immunoconjugate, ADC, or fusion molecule comprising depleting antibodies to specific tumor antigens and a cytotoxic agent, small molecule kinase inhibitor targeted therapy, surgery, radiation therapy, and stem cell transplantation. The combination therapy may be synergistic. The combination therapy may increase the therapeutic index of the anti-cancer therapy.

In various embodiments, the additional therapy comprises administration of an antibody that specifically binds an immune-checkpoint protein antigen from the list including, but not limited to, CD276, CD272, CD152, CD223, CD279, CD274, TIM-3 and B7-H4; or any immune-checkpoint protein antigen antibody taught in the art.

In various embodiments, the PD-1 inhibitor is selected from the group consisting of, but not limited to, nivolumab (Bristol-Myers Squibb) (Drugbank 09035; Drugbank 06132), pembrolizumab (Merck) (Drugbank 09037) and pidilizumab (Medivation) (Drugbank 15383).

In various embodiments, the CTLA-4 inhibitor is selected from the group consisting of, but not limited to, ipilimumab (Bristol-Myers Squibb)(Drugbank 06186) and tremelimumab (MedImmune) (Drugbank 11771).

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

MODE(S) FOR CARRYING OUT THE INVENTION

Definitions

Figure 1:
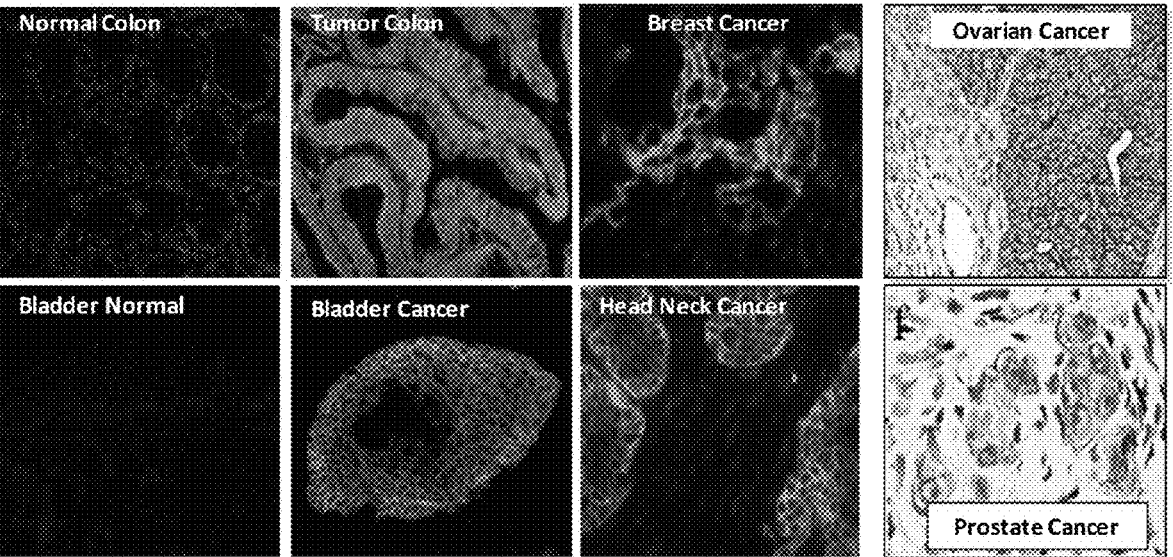
FIG. 1. depicts evaluation of EphB4 expression in epithelial cancers with immunostaining.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

As used herein, a "proliferative disease" includes tumor disease (including benign or cancerous) and/or any metastases. A proliferative disease may include hyperproliferative conditions such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. In various embodiments, the proliferative disease is cancer. In various embodiments, the proliferative disease is a non-cancerous disease. In various embodiments, the proliferative disease is a benign or malignant tumor.

The term "tumor," as used herein, refers to all neoplastic cell growth and proliferation, whether malignant or benign, and all pre-cancerous and cancerous cells and tissues.

The term "primary tumor" refers to all neoplastic cell growth and proliferation, whether malignant or benign, and all pre-cancerous and cancerous cells and tissues located at the anatomical site where the autonomous, unregulated growth of the cells initiated, for example the organ of the original cancerous tumor. Primary tumors do not include metastases.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor (e.g., the organ containing the primary tumor). Metastasis can also be defined as several steps of a process, such as the departure of cancer cells from an original tumor site (e.g., primary tumor site) and migration and/or invasion of cancer cells to other parts of the body.

Tumors of interest for treatment with the methods of the invention include solid tumors, e.g. carcinomas, gliomas, melanomas, sarcomas, and the like. Breast cancer is of particular interest. Carcinomas include a variety of adenocarcinomas, for example in prostate, lung, etc.; adernocartical carcinoma; hepatocellular carcinoma; renal cell carcinoma, ovarian carcinoma, carcinoma in situ, ductal carcinoma, carcinoma of the breast, basal cell carcinoma; squamous cell carcinoma; transitional cell carcinoma; colon carcinoma; nasopharyngeal carcinoma; multilocular cystic renal cell carcinoma; oat cell carcinoma, large cell lung carcinoma; small cell lung carcinoma; etc. Carcinomas may be found in prostrate, pancreas, colon, brain (usually as secondary metastases), lung, breast, skin, etc. Including in the designation of soft tissue tumors are neoplasias derived from fibroblasts, myofibroblasts, histiocytes, vascular cells/endothelial cells and nerve sheath cells. Tumors of connective tissue include sarcomas; histiocytomas; fibromas; skeletal chondrosarcoma; extraskeletal myxoid chondrosarcoma; clear cell sarcoma; fibrosarcomas, etc. Hematologic cancers include leukemias and lymphomas, e.g. cutaneous T cell lymphoma, acute myeloid leukemia (AML), chronic myeloid leukemia (CML), acute lymphoblastic leukemia (ALL), non-Hodgkins lymphoma (NHL), etc.

"Resistant or refractory cancer" refers to tumor cells or cancer that do not respond to previous anti-cancer therapy including, e.g., chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, surgery alone, or combinations thereof. For ease of description and not limitation, it will be understood that the refractory tumor cells are interchangeable with resistant tumor cells.

As used herein, "treatment" is an approach for obtaining beneficial or desired clinical results. For purposes of this invention, beneficial or desired clinical results include, but are not limited to, any one or more of: alleviation of one or more symptoms; diminishment of extent of disease; preventing or delaying spread (e.g., metastasis, for example metastasis to the lung or to the lymph node) of disease; preventing or delaying recurrence of disease; stabilizing, delaying or slowing of disease progression; amelioration of the disease state; remission (whether partial or total); and improving quality of life. Also encompassed by "treatment" is a reduction of pathological consequence of a proliferative disease. The methods of the invention contemplate any one or more of these aspects of treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to NHL and other cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

"Adjuvant setting" refers to a clinical setting in which an subject has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these subjects are considered at risk of development of the disease. Treatment or administration in the "adjuvant setting" refers to a subsequent mode of treatment. The degree of risk (i.e., when an subject in the adjuvant setting is considered as "high risk" or "low risk") depends upon several factors, most usually the extent of disease when first treated.

The phrase "synergistic effect" refers to the effect achieved when the active ingredients used together is greater than the sum of the effects that results from using the active ingredients separately.

The phrase "administering" or "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic regimen, and/or prescribing particular agent(s)/compounds for a subject. Such prescribing can include, for example, drafting a prescription form, annotating a medical record, and the like. Where administration is described herein, "causing to be administered" is also contemplated.

The terms "patient," "subject," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context.

As used herein, the terms "co-administration", "co-administered" and "in combination with", referring to the fusion molecules of the invention and one or more other therapeutic agents, is intended to mean, and does refer to and include the following: simultaneous administration of such combination of fusion molecules of the invention and therapeutic agent(s) to an subject in need of treatment, when such components are formulated together into a single dosage form which releases said components at substantially the same time to said subject; substantially simultaneous administration of such combination of fusion molecules of the invention and therapeutic agent(s) to an subject in need of treatment, when such components are formulated apart from each other into separate dosage forms which are taken at substantially the same time by said subject, whereupon said components are released at substantially the same time to said subject; sequential administration of such combination of fusion molecules of the invention and therapeutic agent(s) to an subject in need of treatment, when such components are formulated apart from each other into separate dosage forms which are taken at consecutive times by said subject with a significant time interval between each administration, whereupon said components are released at substantially different times to said subject; and sequential administration of such combination of fusion molecules of the invention and therapeutic agent(s) to an subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

As used herein, the term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, OX-40, CD137, GITR, LAGS, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF, IFN-$\alpha$, IFN-$\beta$ and IFN-$\gamma$; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

The terms "polypeptide", "peptide" and "protein" are used interchangeably herein to refer to a polymer of amino acid residues. In certain embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free $\alpha$-amino group on an amino acid at the amino terminal of a peptide or to the $\alpha$-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "recombinant polypeptide", as used herein, is intended to include all polypeptides, including fusion molecules that are prepared, expressed, created, derived from, or isolated by recombinant means, such as polypeptides expressed using a recombinant expression vector transfected into a host cell.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)

Aspartic acid (D) and Glutamic acid (E)

Asparagine (N) and Glutamine (Q)

Arginine (R) and Lysine (K)

Isoleucine (I), Leucine (L), Methionine (M), and Valine (V)

Phenylalanine (F), Tyrosine (Y), and Tryptophan (W)

The term "polypeptide fragment" and "truncated polypeptide" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

The term "soluble polypeptide" as used herein merely indicates that the polypeptide does not contain a transmembrane domain or a portion of a transmembrane domain sufficient to compromise the solubility of the polypeptide in a physiological salt solution.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier or excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous and refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

MODE(S) FOR CARRYING OUT THE DISCLOSURE

The methods of the present disclosure include treating, reducing, or preventing primary tumor growth or formation of primary cancer, or metastasis of cancers by administering a polypeptide agent that inhibits EphB4 or EphrinB2 mediated functions, either as monotherapy, or in combination with an PD-1 inhibitor, or other antagonistic, or blocking antibody to an immune checkpoint molecule.

EphB4—EphrinB2 Inhibitors

Type one receptor tyrosine kinase EphB4 and membrane-localized ligand EphrinB2 induce bidirectional signaling (forward in receptor expressing cells, reverse signaling in ligand expressing cells). EphB4 belongs to the largest family of receptor tyrosine kinases and upon interaction with the EphrinB2 ligand has been reported to regulate neuronal migration, bone remodeling, angiogenesis, cancer progression, and metastasis (Pasquale E B, Cell, 133:38-52, 2008). EphB4 and EphrinB2 expression is downregulated in vast majority of adult normal tissues, even as early as postnatal development but EphB4 is over-expressed in multiple epithelial cancers including lung, bladder, head-neck, and pancreatic cancers (Ferguson B D, et el., Growth Factors, 32:202-6, 2014). Oncogenes including mutant Kras and loss of PTEN induce EphB4 expression. Expression of EphB4 correlates with stage, grade and survival since knock down of EphB4 leads to cell death by apoptosis. The ligand EphrinB2's over-expression and correlation with poor outcome have been reported in several cancer types. ICT increases EphrinB2 in the tumor vessels (and tumor) and high EphrinB2 prevents immune cell recruitment and thus resistance to therapy.

Inhibition of the EphB4-EphrinB2 interaction has a direct inhibitory effect on tumor cell proliferation in vitro and ex-vivo. Polypeptide agents that inhibit EphB4 or EphrinB2 mediated functions have been previously described by the present inventors (see, e.g., U.S. Pat. Nos. 7,381,410; 7,862, 816; 7,977,463; 8,063,183; 8,273,858; 8,975,377; 8,981, 062; 9,533,026; each hereby incorporated by reference in their entirety for all purposes). sEphB4-HSA is a fully human fusion protein composed of soluble EphB4 extracellular domain fused at the C-terminus with albumin upon expression as a single seamless protein of 123.3 kDa. sEphB4-HSA specifically binds to EphrinB2. Preliminary studies of sEphB4-HSA in tumor models show increase in T and NK cell migration into tumor. This is accompanied by the induction of ICAM-1 in the tumor vessels. ICAM-1 is an integrin that promotes attachment of T and NK cells to the endothelium followed by transmigration of cells into the tumor. sEphB4-HSA also shows downregulation of PI3K signaling by blocking EphB-EphrinB2 interaction in tumor cell and tumor vessels. sEphB4-HSA blocks the signaling and promote immune cell trafficking into the tumor and inhibit survival signal in tumor cells by downregulating PI3K pathway.

Targeting of EphB4-EphrinB2 represent a therapeutic strategy that has survived the test of clinical trials. It has been shown to be safe in multiple clinical trials with minimal to no toxicity (A. El-Khoueiry B G, et al., Eur J Cancer, 69, 2016), likely due to low levels of expression in normal tissue. While direct evidence that implicates EphB4-EphrinB2 interaction in the cancer-related immune response is lacking, multiple reports have documented that Eph/ephrin gene family members modulate immune cell processes in inflammatory models, such as arteriosclerosis and wound healing (Braun J, et al., Arterioscler Thromb Vasc Biol, 31:297-305, 2011; Poitz D M, et al., Mol Immunol, 68:648-56, 2015; Yu G, et al., J Immunol, 171:106-14, 2003; Funk S D, et al., Arterioscler Thromb Vasc Biol, 32:686-95, 2012). Eph-ephrin interactions have also been reported to regulate monocyte adhesion to the blood vessel wall trans-endothelial migration, T cell chemotaxis, activation, proliferation and apoptosis, and mobilization of hematopoietic cells from bone marrow sinusoids.

In various embodiments of the present invention, the polypeptide agent that inhibits EphB4 or EphrinB2 mediated functions is a monomeric ligand binding portion of the EphB4 protein or EphrinB2 protein, or an antibody that binds to and affects EphB4 or EphrinB2. In various embodiments, the polypeptide agent is a soluble EphB4 (sEphB4) polypeptide that binds specifically to an EphrinB2 polypeptide and comprises an amino acid sequence of an extracellular domain of an EphB4 protein. In various embodiments, the sEphB4 polypeptide comprises a globular domain of an EphB4 protein.

In various embodiments, the sEphB4 polypeptide comprises a sequence selected from the group consisting of a sequence that is at least 90% identical to residues 1-522, at least 90% identical to residues 1-412, and at least 90% identical to residues 1-312 of the amino acid sequence of SEQ ID NO: 1. In various embodiments, the sEphB4 polypeptide may comprise a sequence encompassing the globular (G) domain (amino acids 29-197 of SEQ ID NO; 1), and optionally additional domains, such as the cysteine-rich domain (amino acids 239-321 of SEQ ID NO: 1), the first fibronectin type 3 domain (amino acids 324-429 of SEQ ID NO: 1) and the second fibronectin type 3 domain (amino acids 434-526 of SEQ ID NO: 1). In various embodiments, the sEphB4 polypeptide will comprise amino acids 1-537 of SEQ ID NO: 1. In various embodiments, the sEphB4 polypeptide will comprise amino acids 1-427 of SEQ ID NO: 1. In various embodiments, the sEphB4 polypeptide will comprise amino acids 1-326 of SEQ ID NO: 1. In various embodiments, the sEphB4 polypeptide will comprise amino acids 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537 of SEQ ID NO: 1. In various embodiments, the sEphB4 polypeptide will comprise amino acids 16-197, 16-312, 16-321, 16-326, 16-412, 16-427, 16-429, 16-526 of SEQ ID NO: 1. In various embodiments, a sEphB4 polypeptide may be one that comprises an amino acid sequence at least 90%, and optionally 95% or 99% identical to any of the preceding amino acid sequences while retaining EphrinB2 binding activity. In various embodiments, any variations in the amino acid sequence from the sequence shown in SEQ ID NO: 1 are conservative changes or deletions of no more than 1, 2, 3, 4 or 5 amino acids, particularly in a surface loop region.

In various embodiments, a soluble polypeptide may be prepared in a multimeric form, by, for example, expressing as an Fc fusion protein or fusion with another multimerization domain.

In various embodiments, the sEphB4 polypeptide will further comprise an additional component that confers increased serum half-life while still retaining EphrinB2 binding activity. In various embodiments, the sEphB4 polypeptides are monomeric and are covalently linked to one or more polyoxyaklylene groups (e.g., polyethylene, polypropylene). In various embodiments, the sEphB4 polypeptide is covalently linked to a single polyethylene glycol (PEG) group (hereinafter "sEphB4-PEG"). In various embodiments, the sEphB4 polypeptide is covalently linked to two, three, or more PEG groups.

In various embodiments, the one or more PEG may have a molecular weight ranging from about 1 kDa to about 100 kDa, about 10 to about 60 kDa, and about 10 to about 40 kDa. The PEG group may be a linear PEG or a branched PEG. In various embodiments, the soluble, monomeric sEphB4 conjugate comprises an sEphB4 polypeptide covalently linked to one PEG group of from about 10 to about 40 kDa (monoPEGylated EphB4), or from about 15 to 30 kDa, preferably via an s-amino group of sEphB4 lysine or the N-terminal amino group. In various embodiments, the sEphB4 is randomly PEGylated at one amino group out of the group consisting of the s-amino groups of sEphB4 lysine and the N-terminal amino group.

In various embodiments, the sEphB4 polypeptide is stably associated with a second stabilizing polypeptide that confers improved half-life without substantially diminishing EphrinB2 binding. In various embodiments, the stabilizing polypeptide is immunocompatible with human patients (or animal patients, where veterinary uses are contemplated) and will have little or no significant biological activity. In various embodiments, the sEphB4 polypeptide is associated covalently or non-covalently with an albumin selected from the group consisting of a human serum albumin (HSA) (hereinafter "sEphB4-HSA") and bovine serum albumin (BSA) (hereinafter "sEphB4-BSA").

In various embodiments, the covalent attachment may be achieved by expression of the sEphB4 polypeptide as a co-translational fusion with human serum albumin. The albumin sequence may be fused at the N-terminus, the C-terminus or at a non-disruptive internal position in the sEphB4 polypeptide. Exposed loops of the sEphB4 would be appropriate positions for insertion of an albumin sequence. Albumin may also be post-translationally attached to the sEphB4 polypeptide by, for example, chemical crosslinking. In various embodiments, the sEphB4 polypeptide may also be stably associated with more than one albumin polypeptide.

In various embodiments, the sEphB4-HSA fusion inhibits the interaction between EphrinB2 and EphB4, the clustering of EphrinB2 or EphB4, the phosphorylation of EphrinB2 or EphB4, or combinations thereof. In various embodiments, the sEphB4-HSA fusion has enhanced in vivo stability relative to the unmodified wildtype polypeptide.

In various embodiments, the sEphB4-HSA comprises residues 16-197 of SEQ ID NO: 1 directly fused to residues 25-609 of SEQ ID NO: 2. In various embodiments, the sEphB4-HSA comprises residues 16-312 of SEQ ID NO: 1 directly fused to residues 25-609 of SEQ ID NO: 2. In various embodiments, the sEphB4-HSA comprises residues 16-321 of SEQ ID NO: 1 directly fused to residues 25-609 of SEQ ID NO: 2. In various embodiments, the sEphB4-HSA comprises residues 16-326 of SEQ ID NO: 1 directly fused to residues 25-609 of SEQ ID NO: 2. In various embodiments, the sEphB4-HSA comprises residues 16-412 of SEQ ID NO: 1 directly fused to residues 25-609 of SEQ ID NO: 2. In various embodiments, the sEphB4-HSA comprises residues 16-427 of SEQ ID NO: 1 directly fused to residues 25-609 of SEQ ID NO: 2. In various embodiments, the sEphB4-HSA comprises residues 16-429 of SEQ ID NO: 1 directly fused to residues 25-609 of SEQ ID NO: 2. In various embodiments, the sEphB4-HSA comprises residues 16-526 of SEQ ID NO: 1 directly fused to residues 25-609 of SEQ ID NO: 2. In various embodiments, the sEphB4-HSA comprises residues 16-537 of SEQ ID NO: 1 directly fused to residues 25-609 of SEQ ID NO: 2.

Immune Checkpoint Inhibitors

A number of immune-checkpoint protein antigens have been reported to be expressed on various immune cells, including, e.g., SIRP (expressed on macrophage, monocytes, dendritic cells), CD47 (highly expressed on tumor cells and other cell types), VISTA (expressed on monocytes, dendritic cells, B cells, T cells), CD152 (expressed by activated CD8+ T cells, CD4+ T cells and regulatory T cells), CD279 (expressed on tumor infiltrating lymphocytes, expressed by activated T cells (both CD4 and CD8), regulatory T cells, activated B cells, activated NK cells, anergic T cells, monocytes, dendritic cells), CD274 (expressed on T cells, B cells, dendritic cells, macrophages, vascular endothelial cells, pancreatic islet cells), and CD223 (expressed by activated T cells, regulatory T cells, anergic T cells, NK cells, NKT cells, and plasmacytoid dendritic cells)(see, e.g., Pardoll, D., Nature Reviews Cancer, 12:252-264, 2012). Antibodies that bind to an antigen which is determined to be an immune-checkpoint protein are known to those skilled in the art. For example, various anti-CD276 antibodies have been described in the art (see, e.g., U.S. Pat. Public. No. 20120294796 (Johnson et al) and references cited therein); various anti-CD272 antibodies have been described in the art (see, e.g., U.S. Pat. Public. No. 20140017255 (Mataraza et al) and references cited therein); various anti-CD152/CTLA-4 antibodies have been described in the art (see, e.g., U.S. Pat. Public. No. 20130136749 (Korman et al) and references cited therein); various anti-LAG-3/CD223 antibodies have been described in the art (see, e.g., U.S. Pat. Public. No. 20110150892 (Thudium et al) and references cited therein); various anti-CD279 (PD-1) antibodies have been described in the art (see, e.g., U.S. Pat. No. 7,488,802 (Collins et al) and references cited therein); various anti-PD-L1 antibodies have been described in the art (see, e.g., U.S. Pat. Public. No. 20130122014 (Korman et al) and references cited therein); various anti-TIM-3 antibodies have been described in the art (see, e.g., U.S. Pat. Public. No. 20140044728 (Takayanagi et al) and references cited therein); and various anti-B7-H4 antibodies have been described in the art (see, e.g., U.S. Pat. Public. No. 20110085970 (Terrett et al) and references cited therein). Each of these references is hereby incorporated by reference in its entirety for the specific antibodies and sequences taught therein.

In various embodiments, the immune-checkpoint protein antigen is selected from the group consisting of, but not limited to, PD1 and PDL-1, CD276, CD272, CD152, CD223, CD279, CD274, CD40, SIRPα, CD47, OX-40, GITR, ICOS, CD27, 4-1BB, TIM-3, B7-H3, B7-H4 and VISTA.

Immune checkpoint PD-1 and CTLA inhibitors are efficacious in several cancers which express interferon gamma signature, are rich in tumor infiltrating immune cells and express PD-L1. Tumor vessels regulate immune cell exit into the tumors, thus tumor vessel modulation may offer avenue to change tumor environment.

The PD-1 receptor-ligand interaction is a major pathway hijacked by tumors to suppress immune control. The normal function of PD-1, expressed on the cell surface of activated T-cells under healthy conditions, is to down-modulate unwanted or excessive immune responses, including auto-immune reactions. The ligands for PD-1 (PD-L1 and PD-L2) are constitutively expressed or can be induced in a variety of cell types, including non-hematopoietic tissues as well as in various tumors. Binding of either PD-1 ligand to PD-1 inhibits T-cell activation triggered through the T-cell receptor. PD-1 has been suggested to regulate tumor-specific T-cell expansion in subjects with melanoma (MEL). This suggests that the PD-1/PD-L1 pathway plays a critical role in tumor immune evasion and should be considered as an attractive target for therapeutic intervention.

Pembrolizumab (KEYTRUDA®) is a potent and highly selective humanized monoclonal antibody (mAb) of the IgG4/kappa isotype designed to directly block the interaction between PD-1 and its ligands, PD-L1 and PD-L2. The Food and Drug Administration (FDA) approved KEYTRUDA® on Aug. 5, 2016, for the treatment of some patients with an advanced form of head and neck cancer. The approval is for patients with recurrent or metastatic head and neck squamous cell carcinoma (HNSCC) that has continued to progress despite standard-of-care treatment with chemotherapy. KEYTRUDA® has recently been approved in the United Stated for the treatment of patients with unresectable or metastatic melanoma and disease progression following ipilumumab and, if BRAF V600 mutation positive, a BRAF inhibitor.

Nivolumab (OPDIVO®) is a human IgG4 anti-PD-1 monoclonal antibody that works as a checkpoint inhibitor, blocking a signal that would have prevented activated T cells from attacking the cancer, thus allowing the immune system to clear the cancer. OPDIVO® is used as a first line treatment for inoperable or metastatic melanoma in combination with ipilimumab if the cancer does not have a mutation in BRAF as a second-line treatment following treatment with ipilimumab and if the cancer has a mutation in BRAF, with a BRAF inhibitor as a second-line treatment for squamous non-small cell lung cancer and as a second-line treatment for renal cell carcinoma.

In various embodiments, the PD-1 inhibitor used in the combination therapy methods is selected from the group consisting of, but not limited to, nivolumab (Bristol-Myers Squibb)(Drugbank 09035; Drugbank 06132), pembroli-zumab (Merck)(Drugbank 09037) and pidilizumab (Medivation)(Drugbank 15383).

In various embodiments, the CTLA-4 inhibitor is selected from the group consisting of, but not limited to, ipilimumab (Bristol-Myers Squibb)(Drugbank 06186) and tremelimumab (MedImmune)(Drugbank 11771).

Cancers

Urothelial carcinoma with an incidence of 80,470 cases per year causes 17,670 deaths per year and remains a significant health challenge in the United States (Siegel R L, et al., Cancer J Clin. 2019; 69(1):7-34, 2019). If untreated, the patients have a median survival of ~4.5 months. If treated with cytotoxic chemotherapy, the survival increased to ~7.5 months with ORR of ~15% and PFS of 3-3.5 months. Cytotoxic chemotherapy however results in substantial toxicity. Combination cytotoxic chemotherapy results in modestly improved response rates without improvement in survival, but worsened toxicity. Consequently, before the advent of immunotherapy, for previously treated metastatic urothelial patients, monotherapy has been favored over combination therapy. Most commonly used single agents in the US included gemcitabine, paclitaxel, and docetaxel.

In the metastatic setting the standard of care in the frontline setting has not changed since 2000 and remains cisplatin-based chemotherapy. A number of single agents such as vinflunine (ORR 18%, OS 6.6 months), gemcitabine (ORR 11%, OS 8.7 months), pemetrexed (ORR 28%, OS 9.6 months), paclitaxel (ORR 10%, OS 7.2 months) and combination regimens such as paclitaxel with methotrexate (ORR 32%, OS 5 months) or gemcitabine (ORR 47%, OS 7.5 months) or docetaxel with ifosfamide (ORR 25%, OS 4 months) have been studied after failure of first line therapy. Based on the safety and efficacy, most commonly used agents are paclitaxel, docetaxel, and carboplatin. Response rates are ~10-15% and overall survival of 6-9 months. Combination chemotherapy resulted in higher response rate, greater toxicity, but without improvement in survival (Raggi D, et al., Ann Oncol. 27(1):49-61, 2016). It was not until the approval of anti-PD1/PDL1 antibodies that a more durable second line option with survival benefit became available for previously treated patients with metastatic urothelial carcinoma. With an expected median survival of up to 10.3 months and response rate of 21.1%, 5 different drugs are in clinical practice including pembrolizumab, nivolumab, atezolizumab, avelumab, and durvalumab. Pembrolizumab is approved for this patient population, it is effective in only a minority of the patients having a median overall survival (OS) of 10.3 months (95% CI, 8-11.8), median overall progression free survival (PFS) of 2.1 months (95% CI, 2.0-2.2), with overall response rate (ORR) of 21.1% (95% CI, 16.4 to 26.5), and complete response rate of 7% in this patient population.

Hepatocellular carcinoma (HCC) is the most frequent cancer in certain parts of the world, and the fifth most cancer common worldwide. Globally, it is the second leading cause of cancer death in men and the sixth leading cause of cancer death among women (see, e.g., Parkin D. M., Lancet Oncology, 2:533-43, 2001). Because HCC is often diagnosed late in the course of clinical manifestation, only 10-15% of patients are candidates for curative surgery. For the majority of HCC patients, systemic chemotherapies or supportive therapies are the mainstay treatment options. HCC in general is highly refractory to therapy and most chemotherapeutic agents show limited effectiveness and have not been able to improve patient survival (see, e.g., Gish R. G. et al., J. of Clinical Oncology 25:3069-75, 2007; Ramanathan R.

K. et al., J. of Clinical Oncology 24:4010, 2006). Recent studies evaluating the Programmed Death 1 (PD-1) antibody nivolumab (OPDIVO®) showed response rates of around 10-20%. Response duration was 14-17+ months for CR, <1-8+ months for PR, and 1.5-17+ months for stable disease (SD). Overall survival (OS) rate at 6 months is 72%. Nivolumab demonstrated a manageable AE profile and produced durable responses across all dose levels and HCC cohorts, with a favorable 6-month OS rate.

Head and neck squamous cell carcinoma (HNSCC) accounts for almost 90% of cancers involving the upper aerodigestive tract (UADT). In the United States in 2005, cancers of the oral cavity, pharynx and larynx are expected to account for nearly 3% of incident cancers and 2% of cancer deaths. There are approximately 500,000 new cases diagnosed world-wide each year. Men are affected over two times more than women. Over half of these cancers involve the oral cavity. The rest are divided equally between larynx and pharynx. Numerous clinical trials are testing the benefits of immunotherapy in human cancer, including head and neck squamous cell carcinoma (HNSCC). The objective response rate is 6-20% (Szturz P, et al., BMC Med, 15:110, 2017; Ferris R L, et al., Oral Oncol, 81:45-51, 2018; Postow M A, et al., J Clin Oncol, 33:1974-82, 2015; Chow L Q M, et al., J Clin Oncol, 34:3838-45, 2016; Siu L L, et al., JAMA Oncol 2018) and the vast majority of patients demonstrate either innate or adaptive resistance to immunotherapy. Attempts at simply combining more immune checkpoint inhibitors have also proven disappointing due to increased toxicity to patients and lack of additional benefit (https://clinicaltrials.gov/ct2/show/NCT02205333). In orthotopic mouse models of HNSCC, we have recently demonstrated that tumor regrowth occurs even after combination treatment with anti-PDL1 antibody and radiation therapy (RT) (7,8). Oweida A, et al., Clin Cancer Res, 2018; Messenheimer D J, et al., Clin Cancer Res, 23:6165-77, 2017).

Radiation therapy remains the standard of care treatment in the definitive management of patients with locally advanced HNSCCs and can act as an adjuvant for immunotherapy but there are some undesirable effects mounted in response to RT that in turn compromises the efficacy of immunotherapeutic agents. RT is unable to overcome the accumulation of immunosuppressive populations such as Tregs in the later (repair) phase (7). Therefore, finding other treatments that synergize with RT and counteract its negative effects is critical to overcome adverse side-effects, treatment resistance, and tumor regrowth.

Five-year survival rates for HNSCC are low and have not improved in several decades. Moreover, patients with this disease experience severe morbidity including disfigurement, speech, swallowing and breathing problems. Late stage of diagnosis and propensity to recur are challenges that thwart efforts to improve outcomes in these patients. Pembrolizumab is a potent and highly selective humanized monoclonal antibody (mAb) of the IgG4/kappa isotype designed to directly block the interaction between PD-1 and its ligands, PD-L1 and PD-L2. The Food and Drug Administration (FDA) approved pembrolizumab (KEYTRUDA®) on Aug. 5, 2016, for the treatment of some patients with an advanced form of head and neck cancer. The approval is for patients with recurrent or metastatic head and neck squamous cell carcinoma (HNSCC) that has continued to progress despite standard-of-care treatment with chemotherapy. According to the FDA approval summary, 28 patients (16%) experienced a tumor response following treatment with pembrolizumab. In 23 (82%) of those patients, the tumor response lasted for 6 months or longer, and several have lasted for more than 2 years. Patients with HNSCC whose tumors are positive for the human papillomavirus (HPV) typically have better outcomes after treatment with chemotherapy than patients whose tumors are HPV negative. According to the FDA approval summary, responses were seen in patients with HPV-positive tumors as well as in patients with HPV-negative tumors (24% and 16%, respectively).

Non-small cell lung cancer (NSCLC) is the most common type of lung cancer. Squamous cell carcinoma, adenocarcinoma, and large cell carcinoma are all subtypes of NSCLC. NSCLC accounts for about 85% of all lung cancers. As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy). On Oct. 2, 2015, the FDA approved pembrolizumab for the treatment of metastatic non-small cell lung cancer (NSCLC) in patients whose tumors express PD-L1 and who have failed treatment with other chemotherapeutic agents. In October 2016, pembrolizumab became the first immunotherapy to be used first line in the treatment of NSCLC if the cancer overexpresses PDL1 and the cancer has no mutations in EGFR or in ALK; if chemotherapy has already been administered, then pembrolizumab can be used as a second line treatment but if the cancer has EGFR or ALK mutations, agents targeting those mutations should be used first. Assessment of PDL1 must be conducted with a validated and approved companion diagnostic. In the Keynote-001 trial (NTC01295827), the efficacy and safety of programmed cell death 1 (PD-1) inhibition with pembrolizumab was assessed in patients with advanced non-small-cell lung cancer. Among all the patients, the objective response rate was 19.4%, and the median duration of response was 12.5 months. The median duration of progression-free survival was 3.7 months, and the median duration of overall survival was 12.0 months. PD-L1 expression in at least 50% of tumor cells was selected as the cutoff from the training group. Among patients with a proportion score of at least 50% in the validation group, the response rate was 45.2%. Among all the patients with a proportion score of at least 50%, median progression-free survival was 6.3 months; median overall survival was not reached. PD-L1 expression in at least 50% of tumor cells correlated with improved efficacy of pembrolizumab (Garon et al., N Engl J Med, 372:2018-2028, 2015)

Prostate cancer is the most common non-cutaneous malignancy in men and the second leading cause of death in men from cancer in the western world. Prostate cancer results from the uncontrolled growth of abnormal cells in the prostate gland. Once a prostate cancer tumor develops, androgens, such as testosterone, promote prostate cancer tumor growth. At its early stages, localized prostate cancer is often treated with local therapy including, for example, surgical removal of the prostate gland and radiotherapy. However, when local therapy fails to cure prostate cancer, as it does in up to a third of men, the disease progresses into incurable metastatic disease (i.e., disease in which the cancer has spread from one part of the body to other parts). As used herein, the term "prostate cancer" is used in the broadest sense and refers to all stages and all forms of cancer arising from the tissue of the prostate gland. The term "prostate cancer" encompasses any type of malignant (i.e. non-benign) tumor located in prostatic tissues, such as e.g. prostatic adenocarcinoma, prostatic sarcoma, undifferentiated prostate cancer, prostatic squamous cell carcinoma, prostatic ductal transitional carcinoma and prostatic intraepithelial neoplasia.

Kaposi sarcoma (KS) is a multifocal angioproliferative disorder of vascular endothelium, most associated with infection with the Kaposi-sarcoma associated herpes virus (KSHV), also known as human herpes virus-8 (HHV-8). KS is associated with a number of epidemiologic and pathophysiologic factors. KS is classified into four distinct clinical types: classic Mediterranean KS, African-endemic KS, immunosuppressive drug-related KS, and HIV-related KS. A rare disease before the era of HIV and AIDS, HIV-related KS is the most frequent malignancy in HIV infected patients. KS can affect many organs. KS manifests most frequently as a disease of the skin. In many advanced cases, KS involves organs such as the lungs, liver, or gastrointestinal tract. At this time, KS is incurable. Available therapies are for palliation. Systemic chemotherapy is generally used for patients with more advanced disease or evidence of rapid progression of disease. The major goals of treatment are symptom palliation, prevention of disease progression, and reduction of tumor burden to alleviate lymphedema, organ compromise, and psychological stress. The standard therapies for visceral or advanced cutaneous KS include cytotoxic chemotherapy such as liposomal anthracycline and paclitaxel. Liposomal doxorubicin has superior efficacy and favorable tolerability and toxicity compared to the combination of non-liposomal doxorubicin, vincristine, and bleomycin with overall response rates of 59% in HIV patients. In classical KS, response rates to liposomal doxorubicin can be higher. However, complete response rates are uncommon and there is no cure. At this point in time, no targeted therapy has been fully developed for KS.

In 2014, it is projected that 46,420 new cases of pancreatic cancer will be diagnosed in the United States, with an estimated 39,590 deaths from the disease. Although surgical resection is the only potentially curative treatment modality, only 15-20% of patients have respectable disease at diagnosis, and the treatment for unresectable, locally advanced, and metastatic pancreatic cancer remains largely palliative. Gemcitabine monotherapy has been used as the reference regimen for treatment of advanced pancreatic cancer after a randomized trial showed a clinical benefit as well as a survival benefit of about one month when compared to single-agent fluorouracil. Combination therapy with gemcitabine-based regimens for locally advanced and metastatic pancreatic cancer was shown in a meta-analysis to provide a slight benefit in overall survival (OS), albeit with more frequent toxicities, and there is also evidence to suggest an improved benefit with combination regimens in patients with good performance status. One such combination regimen is gemcitabine plus albumin-bound paclitaxel (nab-paclitaxel). In the phase 3 open-label MPACT trial, 861 patients were randomized in a 1:1 ratio to receive either intravenous infusions of gemcitabine (1000 mg per square meter body surface area or mg/m²) alone or gemcitabine (1000 mg/m²) plus nab-paclitaxel (125 mg/m²). The combination group had an increased median overall survival of 8.5 months as compared to 6.7 months in the single agent group, but more high-grade neutropenia, fatigue, and neuropathy were seen in the former. In the combination group, 41% of patients had dose-reductions of nab-paclitaxel, and 47% had dose reductions of gemcitabine. Because of the 1.8 month increase in OS, this study led to the 2013 Food and Drug Administration (FDA) approval of nab-paclitaxel for the treatment of late-stage pancreatic cancer. An updated OS analysis of the MPACT study published in 2015 confirmed a longer median OS of 8.7 months in the nab-paclitaxel and gemcitabine combination group, compared to 6.6 months in the gemcitabine monotherapy group.

In various embodiments, the cancer is selected from the group consisting of, but not limited to, non-small cell lung carcinoma (NSCLC), colon carcinoma, metastatic urothelial cancer, breast cancer, hepatocellular carcinoma (HCC), mesothelioma, pancreatic cancer, prostate cancer, bladder cancer, squamous cell carcinoma of the head and neck (HNSCC), Kaposi sarcoma, and leukemia.

In various embodiments, the patient previously responded to treatment with an anti-cancer therapy, but, upon cessation of therapy, suffered relapse (hereinafter "a recurrent proliferative disease").

In various embodiments, the patient has resistant or refractory cancer. In various embodiments, the cancer is refractory to immunotherapy treatment. In various embodiments, the cancer is refractory to treatment with a chemotherapeutic agent. In various embodiments, the cancer is refractory to treatment using depleting antibodies to specific tumor antigens. In various embodiments, the cancer is refractory to treatment using agonistic, antagonistic, or blocking antibodies to co-stimulatory or co-inhibitory molecules (immune checkpoints). In various embodiments, the cancer is refractory to targeted treatment with an immunoconjugate, antibody-drug conjugate (ADC), or fusion molecule comprising a depleting antibody to a specific tumor antigen and a cytotoxic agent. In various embodiments, the cancer is refractory to targeted treatment with a small molecule kinase inhibitor. In various embodiments, the cancer is refractory to combination therapy involving, for example, two or more of: immunotherapy treatment, treatment with a chemotherapeutic agent, treatment using depleting antibodies to specific tumor antigens, treatment using agonistic, antagonistic, or blocking antibodies to co-stimulatory or co-inhibitory molecules (immune checkpoints), treatment with a immunoconjugate, ADC, or fusion molecule comprising a depleting antibody to a specific tumor antigen and a cytotoxic agent, targeted treatment with a small molecule kinase inhibitor, treatment using surgery, treatment using stem cell transplantation, and treatment using radiation.

Pharmaceutical Compositions

In various embodiments, the polypeptide therapeutic agents of the present invention are often administered as pharmaceutical compositions comprising an active therapeutic agent, i.e., and a variety of other pharmaceutically acceptable components. (See Remington's Pharmaceutical Science, 15.sup.th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In various embodiments, pharmaceutical compositions for the treatment of primary or metastatic cancer can be administered by parenteral, topical, intravenous, intratumoral, oral, subcutaneous, intraarterial, intracranial, intraperitoneal, intranasal or intramuscular means.

For parenteral administration, pharmaceutical compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. Typically, the pharmaceutical compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The polypeptide agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

In various embodiments, methods of the present invention include administering to a patient in need of treatment a therapeutically effective amount or an effective dose of sEphB4-HSA polypeptide of the present invention. In various embodiments, effective doses of the polypeptides of the present invention, e.g. for the treatment of primary or metastatic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

In various embodiments, the dosage may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. In various embodiments, the dosage of the polypeptide administered to the patient is selected from the group consisting of about 0.5, of about 1.0, of about 1.5, of about 2.0, of about 2.5, of about 3.0, of about 3.5, of about 4.0, of about 4.5, of about 5.0, of about 6.0, of about 7.0, of about 8.0, of about 9.0, and of about 10.0 mg/kg. In various embodiments, the treatment regime entails administration once per every two weeks or once a month or once every 3 to 6 months. Therapeutic entities of the present invention are usually administered on multiple occasions. Intervals between single dosages can be weekly, bi-weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Toxicity of the polypeptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from the cell culture assays and animal studies can be used in formulating a dosage range that is not toxic for use in human. The dosage of the polypeptides described herein lies preferably within a range of circulating concentrations that include the effective dose with little or no toxicity. The dosage can vary within this range depending upon the dosage form employed and the route of administration utilized. The exact formulation, route of administration and dosage can be chosen by the subject physician in view of the patient's condition. (See, e.g., Fingl et al., 1975, In: The Pharmacological Basis of Therapeutics, Ch. 1).

In various embodiments, the methods comprise one or more additional anti-cancer therapies selected from the group consisting of immunotherapy, chemotherapy, targeted treatment using depleting antibodies to specific tumor antigens, targeted treatment using agonistic, antagonistic, or blocking antibodies to co-stimulatory or co-inhibitory molecules (immune checkpoints), targeted treatment with an immunoconjugate, ADC, or fusion molecule comprising depleting antibodies to specific tumor antigens and a cytotoxic agent, small molecule kinase inhibitor targeted therapy, surgery, radiation therapy, and stem cell transplantation. The combination may be synergistic. The combination may increase the therapeutic index of the anti-cancer therapy.

In various embodiments, the immunotherapy is selected from the group consisting of: treatment using agonistic, antagonistic, or blocking antibodies to co-stimulatory or co-inhibitory molecules (immune checkpoints) such as CTLA-4, PD-1, OX-40, CD137, GITR, LAGS, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF and IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod. In various embodiments, the immunotherapy is selected from the group consisting of: treatment using agonistic, antagonistic, or blocking antibodies to co-stimulatory or co-inhibitory molecules; treatment using chimeric antigen receptor (CAR)-T cells; treatment using CAR-NK cells; and treatment using bispecific T cell engaging antibodies (BiTE®). In various embodiments, the immunotherapy is treatment using agonistic, antagonistic, or blocking antibodies to co-stimulatory or co-inhibitory molecules. In various embodiments, the immunotherapy is treatment using chimeric antigen receptor (CAR)-T cells. In various embodiments, the immunotherapy is treatment using CAR-NK cells. In various embodiments, the immunotherapy is treatment using bispecific T cell engaging antibodies (BiTE®).

In various embodiments, the additional therapy comprises an antibody that specifically binds an immune-checkpoint protein antigen from the list including, but not limited to, CD276, CD272, CD152, CD223, CD279, CD274, TIM-3 and B7-H4; or any immune-checkpoint protein antigen antibody taught in the art. In various embodiments, the PD-1 inhibitor used in the combination therapy methods is selected from the group consisting of, but not limited to, pembrolizumab (Merck), nivolumab (Bristol-Myers Squibb), and pidilizumab (Medivation). In various embodiments, the PD-1 inhibitor is pembrolizumab. In various embodiments, the PD-1 inhibitor is nivolumab. In various embodiments, the PD-1 inhibitor is pidilizumab.

In various embodiments, between about 0.1 mg/kg to about 10 mg/kg of PD-1 inhibitor is administered. In various embodiments, between about 1 mg/kg to about 15 mg/kg of PD-1 inhibitor is administered. In various embodiments, between about 3 mg/kg to about 12 mg/kg of PD-1 inhibitor is administered. In various embodiments, between about 1 mg/kg to about 10 mg/kg of PD-1 inhibitor is administered. In various embodiments, between about 3 mg/kg to about 10 mg/kg of PD-1 inhibitor is administered. In various embodiments, at least about 1 mg/kg of PD-1 inhibitor is administered. In various embodiments, at least about 2 mg/kg of PD-1 inhibitor is administered. In various embodiments, at least about 3 mg/kg of PD-1 inhibitor is administered. In various embodiments, at least about 5 mg/kg of PD-1 inhibitor is administered. In various embodiments, at least about 10 mg/kg of PD-1 inhibitor is administered. In various embodiments, between about 10 mg to about 400 mg of PD-1 inhibitor is administered. In various embodiments, between about 50 mg to about 400 mg of PD-1 inhibitor is administered. In various embodiments, between about 10 mg to about 300 mg of PD-1 inhibitor is administered. In various embodiments, between about 50 mg to about 300 mg of PD-1 inhibitor is administered. In various embodiments, between about 10 mg to about 250 mg of PD-1 inhibitor is administered. In various embodiments, between about 50 mg to about 250 mg of PD-1 inhibitor is administered. In various embodiments, at least about 50 mg of PD-1 inhibitor is administered. In various embodiments, at least about 100 mg of PD-1 inhibitor is administered. In various embodiments, at least about 150 mg of PD-1 inhibitor is administered. In various embodiments, at least about 200 mg of PD-1 inhibitor is administered. In various embodiments, at least about 250 mg of PD-1 inhibitor is administered. In various embodiments, at least about 300 mg of PD-1 inhibitor is administered. In various embodiments, the PD-1 inhibitor is administered at least once during a cycle. In various embodiments, the PD-1 inhibitor is administered at least twice during a cycle. In various embodiments, a cycle is 21 days. In various embodiments, a cycle is 28 days. In various embodiments, the PD-1 inhibitor is administered at least once a week. In various embodiments, the PD-1 inhibitor is administered at least once every two weeks. In various embodiments, the PD-1 inhibitor is administered at least once every three weeks. In various embodiments, the PD-1 inhibitor is administered at least once every four weeks.

Depending on the nature of the combinatory therapy, administration of the polypeptide therapeutic agents of the invention may be continued while the other therapy is being administered and/or thereafter. The polypeptide therapeutic agents may be administered prior to, concurrently with, or following the additional anti-cancer therapy, usually within at least about 1 week, at least about 5 days, at least about 3 days, at least about 1 day. The polypeptide therapeutic agents may be delivered in a single dose, or may be fractionated into multiple doses, e.g. delivered over a period of time, including daily, bidaily, semi-weekly, weekly, etc. The effective dose will vary with the route of administration, the specific agent, the dose of anti-cancer agent, and the like, and may be determined empirically by one of skill in the art.

The following examples are provided to describe the disclosure in further detail.

Example 1

EphB4 Expression in Epithelial Cancers

The expression of EphB4 in human tumors has been analyzed with an immunostaining assay. Fresh frozen tumor samples and, when possible, adjacent normal tissues were analyzed for EphB4 expression using the EphB4-specific monoclonal antibody MAb131. EphB4 expression was induced in many of the epithelial cancers analyzed (summarized in Table 1). For example, EphB4 is not expressed in the normal bladder and colon but is highly expressed in the bladder and colon tumors. The representative cases of EphB4 expression in breast cancer, head and neck cancer, ovarian cancer, and prostate cancer are also shown in FIG. 1.

TABLE 1

| Tissue of Origin | # of Tumors Studied | # expressing EphB4 (%) |
|---|---|---|
| Head and Neck | 41* | 41 (100%) |
| Lung | 110* | 72 (66%) |
| Esophagus | 25 | 19 (76%) |
| Bladder | 35 | 33 (94%) |
| Prostate | 62 | 41 (66%) |
| Breast | 23 | 19 (82%) |
| Colorectal | 102 | 102 (100%) |
| Ovary | 85 | 73 (86%) |

*Gene amplification was found and is described below

EphB4 gene amplification was analyzed in head and neck cancer, lung cancer, and esophageal cancer. In esophagus squamous cell carcinoma, 9 of 15 (60%) patients had a gene copy number between 4 and 20. Similarly, in esophagus adenocarcinoma, 5 of 8 (62%) had gene copy number ranging from 4 to 20.

Example 2

Inhibition of EphB4-EphrinB2 Signaling Reprograms the Tumor Immune Microenvironment in Various Cancers EphrinB2 is a gatekeeper of immune cell trafficking in the tumor. Studies were performed to evaluate the effects of inhibiting EphB4-EphrinB2 signaling as relates to the tumor microenvironment and on immune cell trafficking.

Figures 2A, 2B, 2C, 2D, 2E, 2F, 2G:
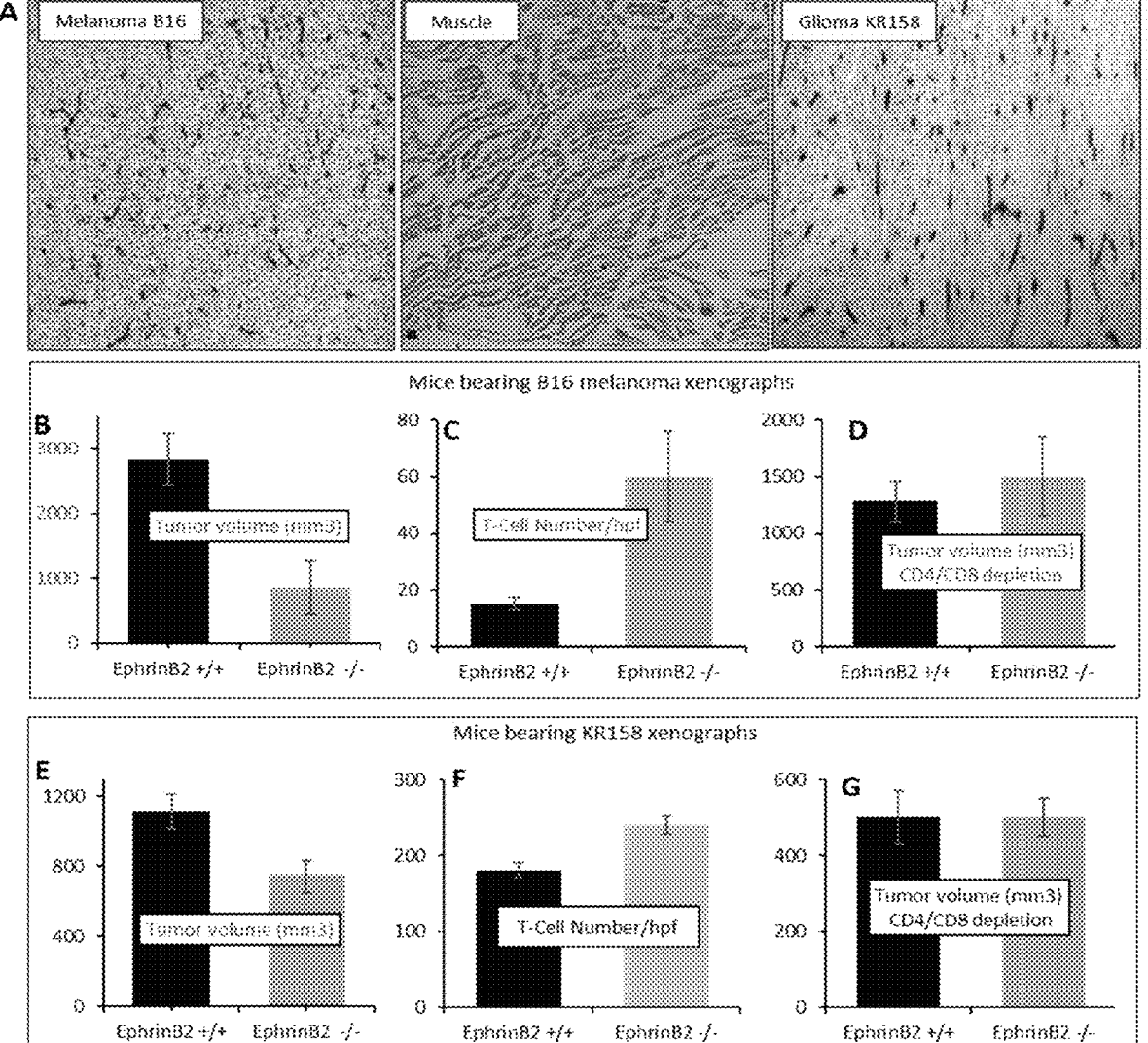
FIG. 2A depicts EphrinB2 expression in the tumor vessel in EphrinB2-LacZ mice bearing B16 melanoma (Left) or glioma KR158 (Right), or normal muscle as a control (Center).
FIG. 2B depicts EphrinB2 conditional knock out mice bearing B16 melanoma show reduced tumor growth compared to wild type mice.
FIG. 2C depicts EphrinB2 conditional knock out mice bearing B16 melanoma have increase in CD3+ T cell numbers compared to wild type mice.
FIG. 2D depicts depletion of CD4/CD8 T cells abolish the decrease in tumor growth in EphrinB2 conditional knock out mice.
FIG. 2E depicts EphrinB2 conditional knock out mice implanted with KR158 show reduced tumor growth.
FIG. 2F depicts tumors harvested from the previous experiment show increase in CD3+ T cell numbers in EphrinB2 conditional knock out mice compared to wild type mice.
FIG. 2G depicts mice treated with CD4/CD8 depleting antibody show similar tumor growth in EphrinB2 conditional knock out and wild type mice.
Figure 3:
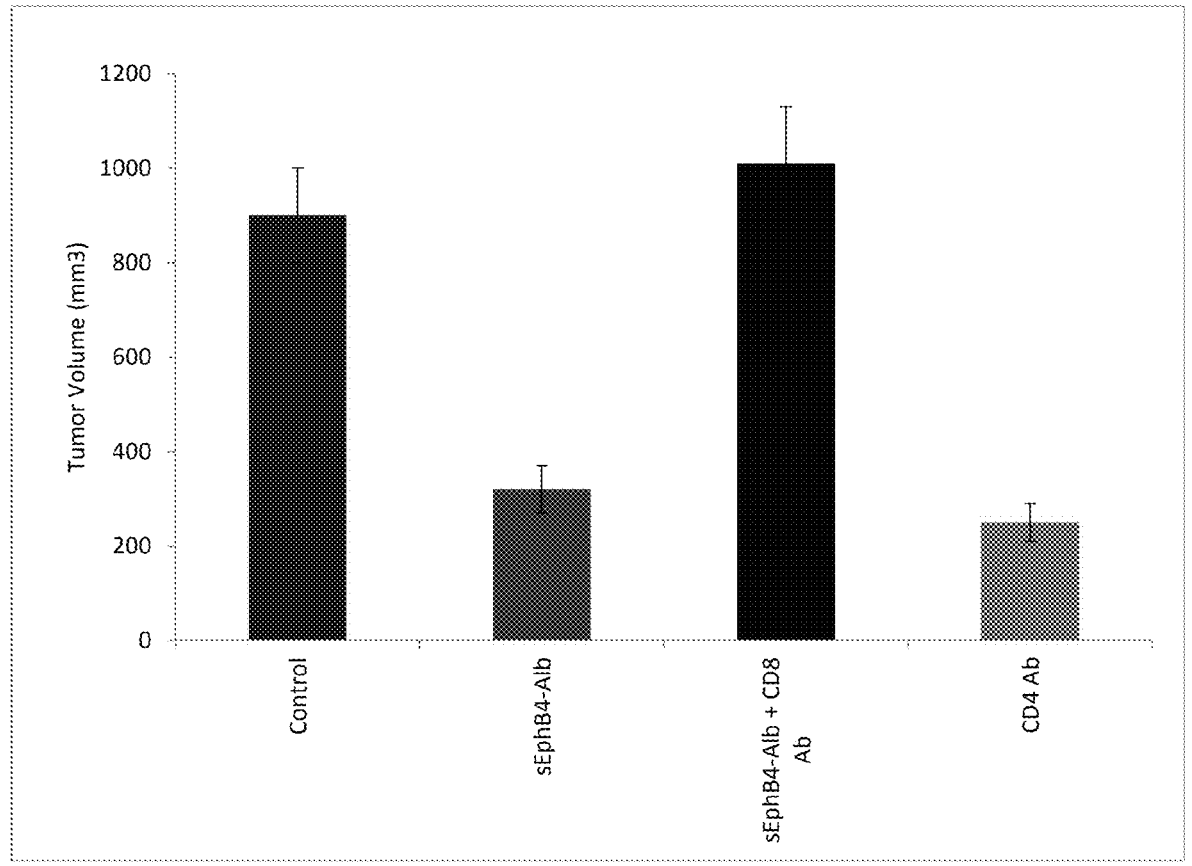
FIG. 3 depicts that msEphB4-MSA tumor growth inhibitory effect on B16 melanoma is abolished with CD8 cell depletion but not CD4 cell depletion.

Mouse analog of sEphB4 fused to Mouse Serum Albumin (msEphB4-MSA) was used in all mice-studies in order to prevent immune response to the drug. Mice treated with msEphB4-MSA did not elicit antibody response to the protein. Tumor cells were injected either subcutaneously or intravenously into EphrinB2$^{lacZ/WT}$ mice and tissues were analyzed using x-gal staining. EphrinB2 expression was observed in tumor vasculature of all syngeneic tumors (B16, KR158, LLC, EL4) as well as spontaneous lymphoma. Normal adjacent and vital organs such as liver, lack EphrinB2 expression (FIG. 2A). EphrinB2 conditional knock out mice bearing B16 melanoma show reduced tumor growth compared to wild type mice (FIG. 2B). EphrinB2 conditional knock out mice bearing B16 melanoma have increase in CD3+ T cell numbers compared to wild type mice (FIG. 2C). Depletion of CD4/CD8 T cells abolish the decrease in tumor growth in EphrinB2 conditional knock out mice (FIG. 2D). EphrinB2 conditional knock out mice implanted with KR158 show reduced tumor growth (FIG. 2E). Tumors harvested from the previous experiment show increase in CD3+ T cell numbers in EphrinB2 conditional knock out mice compared to wild type mice (FIG. 2F). Mice treated with CD4/CD8 depleting antibody show similar tumor growth in EphrinB2 conditional knock out and wild type mice (FIG. 2G).

msEphB4-MSA fusion protein targets EphrinB2 and blocks its binding to EphB receptors and arrests bidirectional signaling. msEphB4-MSA inhibits tumor growth and promotes immune cell migration into the tumor. Depletion of CD8 cells (not CD4 cells) abolishes the tumor growth inhibitory effect of sEphB4-MSA (FIG. 3). These studies demonstrate that recruitment of T cells in tumors is regulated by EphrinB2 in tumor vessels.

In order to understand the mechanism of T cell recruitment by msEphB4-MSA, we conducted unbiased gene expression analysis on CD45 selected T cells. A panel of 770 tumor immune-related gene expression analysis showed induction of inflammatory pathway, dendritic cell maturation pathway, upregulation of NF-kB pathway. Gene expression analysis showed T cell exhaustion and co-stimulatory gene induction including PD-1, PD-L1, PD-L2, CD80, CD27, CTLA-4, MARCO, EOMES, TIGIT, ICOS, OX40 and others.

Figure 4:
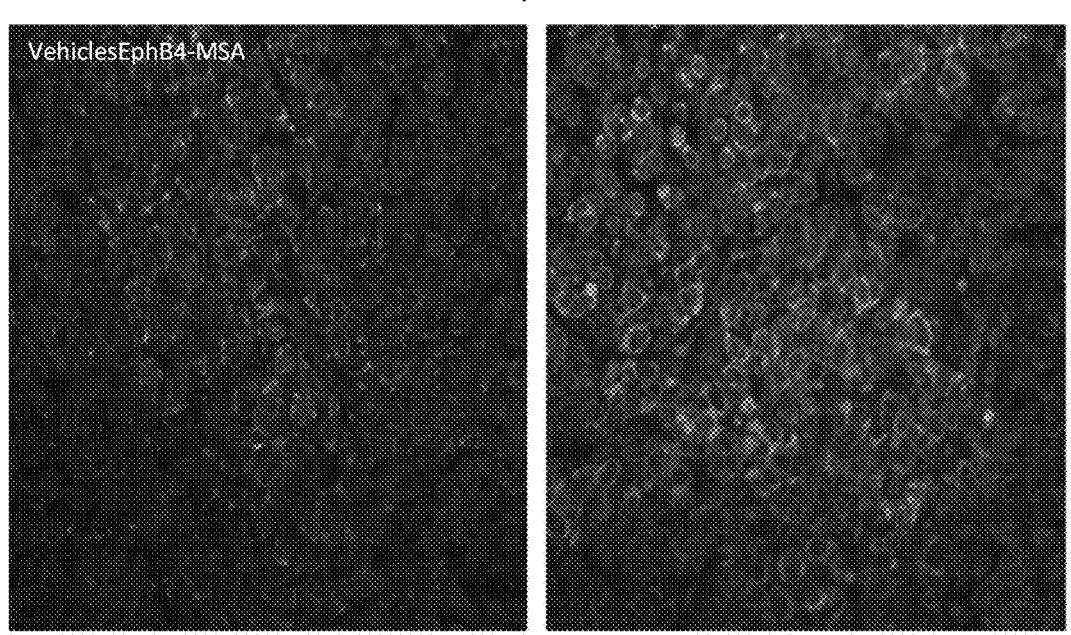
FIG. 4 depicts msEphB4-MSA treatment inducing PD-L1 expression. Tumor samples from control and mouse sEphB4-MSA treated tumors were analyzed for PD-L1 expression by immunofluorescence. PD-L1 localization in the membrane is seen.

PD-L1 induction with mouse sEphB4-MSA treatment was confirmed in tumor samples from msEphB4-MSA and control mice bearing B16 melanoma, as shown below (FIG. 4).

Figure 5:
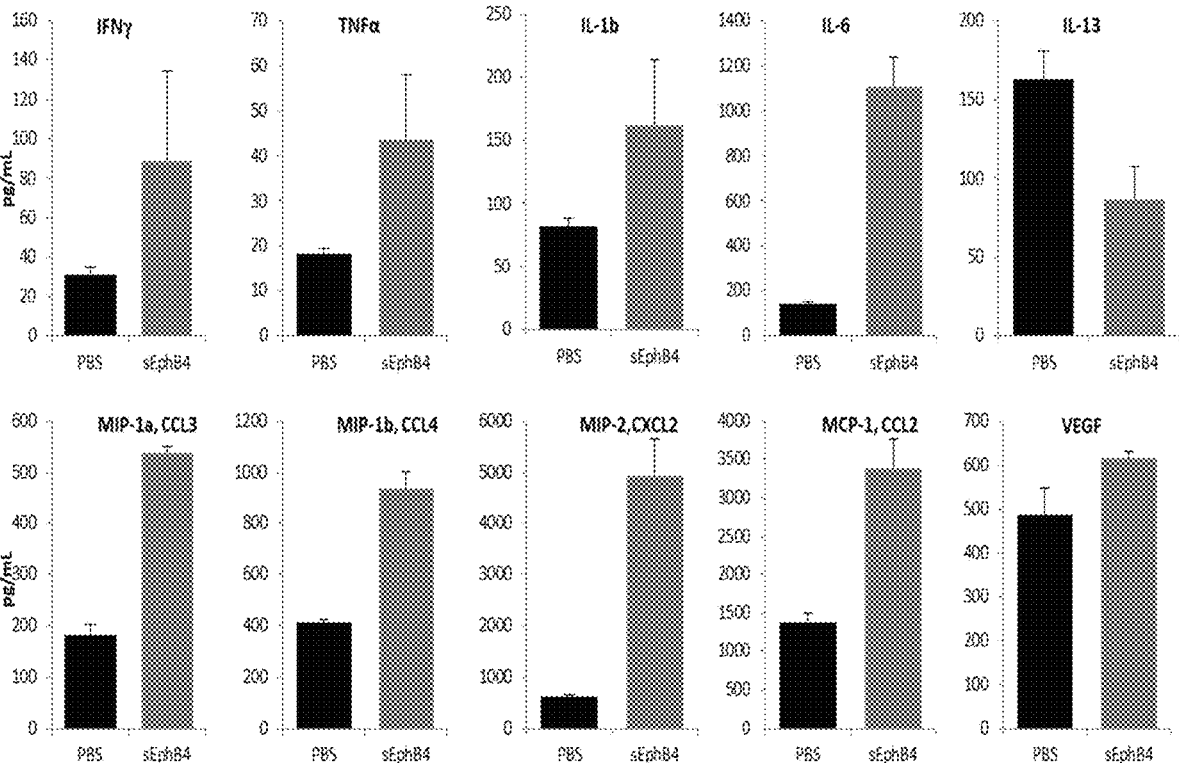
FIG. 5 depicts the analysis of cytokines and chemokines in B16 melanoma tumor lysates after EphB4-Alb therapy.

B16 melanoma tumor lysates were also analyzed for cytokines and chemokines. Tumors from msEphB4-MSA treated mice showed significant increase in TNF-α, interferon gamma, IL-1, IL-6, MIPa, MIP1b, MCP-1 consistent with inflammatory response in the tumor (FIG. 5).

In order to study the mechanism regulating T cell emigration into the tumor, we analyzed a tumor immune cell panel of 770 genes from 24 different cell types, which include common check point inhibitors, CT antigens and genes covering both the innate and adaptive immune response. Normally immune cells roll along the vascular endothelium, but presence of ICAM-1 tethers the immune cells by engaging LFA-1 (Yang L, et al., Blood, 106(2):584-592, 2005). This interaction activates immune cells and promotes emigration into extravascular space. In order to validate this process, we treated tumor bearing mice with ICAM-1 antibody. After exposure of mice to ICAM-1 antibody, mice treated with msEphB4-MSA had tumor growth comparable to control mice. Specifically, tumor growth inhibition with msEphB4-MSA tumor inhibitory activity was markedly reduced in mice receiving ICAM-1 antibody treatment indicating that ICAM-1 induction is required for trafficking immune cells from the circulation into the tumor. These data support the role of ICAM-1 in immune cell trafficking in response to msEphB4-MSA and demonstrates that msphB4-MSA treatment induces ICAM-1 to regulate immune cell trafficking.

Figure 6:
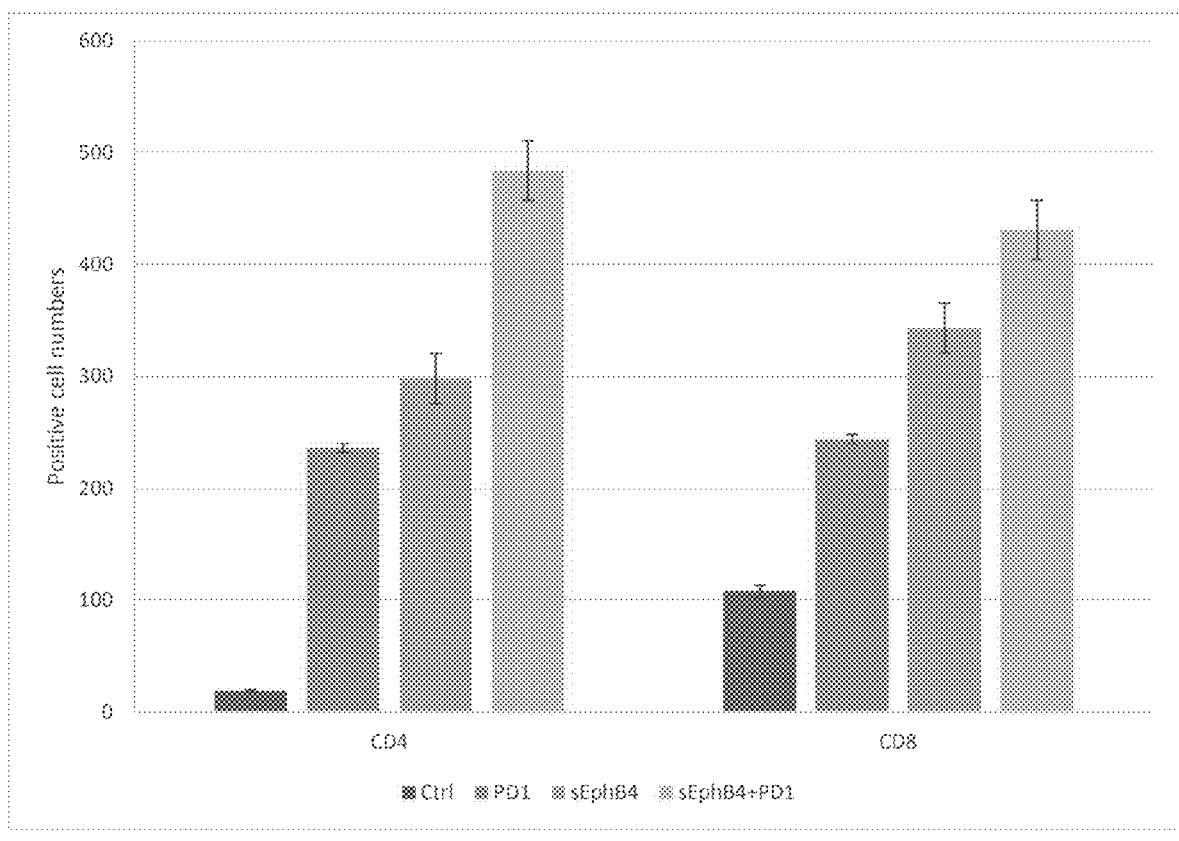
FIG. 6 depicts quantitation of CD4 and CD8 T cells.

Gene expression studies in tumor infiltrating immune cells (CD45+) revealed induction of PD-L1, PD-L2, and PD-1. Induction of PD-L1 suggests a feedback inhibition of msEphB4-MSA activity. We thus tested the combination of PD-1 antagonistic antibody and msEphB4-MSA in mouse model. C57B16 mice bearing B16 melanoma cells were treated with control PBS, sEphB4-MSA, PD-1 antibody or combination therapy. Tumor volume was measured over time. sEphB4-MSA plus PD-1 antibody enhance antitumor activity and recruitment of immune cells and combination therapy was more effective than each compound alone. Tumors were stained for CD4 or CD8 and combination therapy showed greatest increase in T cell localization into the tumor. Quantitation of CD4 and CD8 T cells shows the highest increase with combination therapy (FIG. 6).

Figure 7:
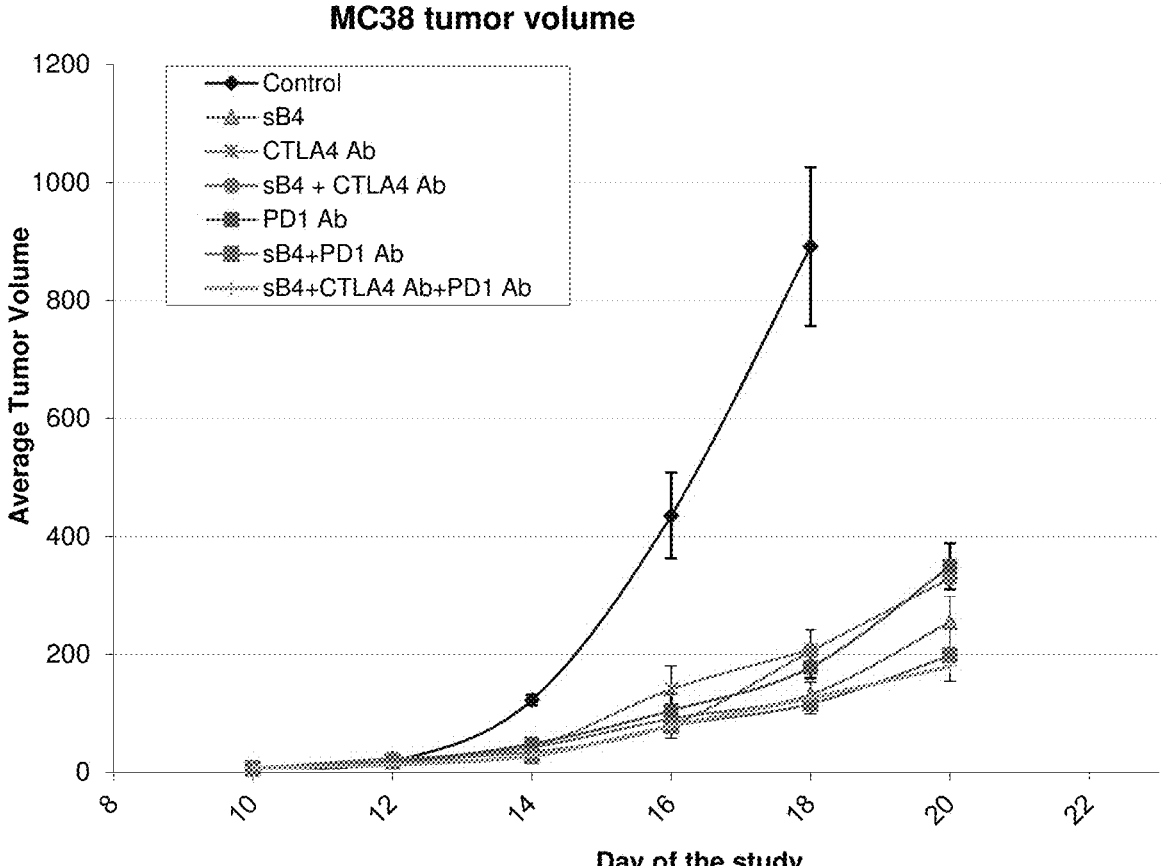
FIG. 7 depicts tumor volume of B16 melanoma tumors treated with sEphB4 10 mg/kg three times a week, and PD-1 neutralizing antibody 100 μg twice a week, CTLA 4 antibody at 100 μg twice a week intraperitoneally for 10 days. Tumor volume is measured over time.

B16 melanoma cells were implanted in C57/B6 immune competent mice. When the tumors reach a volume of around 100 mm$^3$, mice were treated with sEphB4 10 mg/kg three times a week, and PD-1 neutralizing antibody 100 μg twice a week, CTLA 4 antibody at 100 μg twice a week intraperitoneally for 10 days. Tumor volume is measured over time. sEphB4 promotes T cell infiltration and markedly reduces tumor volume. This effect is further enhanced in combination with PD-1 antibody and with CTLA-4 antibody (FIG. 7).

TABLE 2

| Tumor Volume | Day 10 mm3 | Day 12 mm3 | Day 14 mm3 | Day 16 mm3 | Day 18 mm3 |
|---|---|---|---|---|---|
| Control | 6.9 | 19 | 122.7 | 435.4 | 891.3 |
| sB4 | 6.3 | 18 | 42.7 | 91.1 | 131.9 |
| CTLA4 Ab | 8.6 | 18.8 | 43.2 | 140.5 | 207.8 |
| sB4 + CTLA4 Ab | 6.4 | 23.7 | 34.6 | 80.2 | 205.4 |
| PD1 Ab | 6.1 | 18 | 48.2 | 104.8 | 178.3 |
| sB4 + PD1 Ab | 7 | 18.2 | 26.9 | 78.4 | 116.2 |
| sB4 + CTLA4 Ab + PD1 Ab | 8 | 13.1 | 28.6 | 78.5 | 126 |

These studies demonstrate that sEphB4-HSA blocks EphrinB2 signaling to alter tumor microenvironment, promotes T cell recruitment, induces PD-L1/PD-1 and primes enhanced efficacy when combined with PD-1 antagonistic antibody and CTLA-4 antibody. This experimental data supports the role of EphrinB2 in preventing recruitment of T cells into the tumor.

Example 3

An sEphB4-HSA phase I dose escalation study was completed without reaching a maximal tolerated dose (MTD). sEphB4-HSA demonstrated single agent activity in certain tumor types including Head Neck Squamous Cell Carcinoma, Hepatocellular Carcinoma and Kaposi's Sarcoma. sEphB4-HSA was well tolerated, with notable increased frequency of hypertension as a drug related toxicity. sEphB4-HSA single agent trial showed increase in T cell recruitment into the tumor, as well as induction of ICAM-1 in tumor vessels.

Example 4

This example describes a Phase II clinical trial of sEphB4-HSA in combination with pembrolizumab. Eligibility criteria for patients were locally advanced or metastatic urothelial cancer, who had previously failed (relapsed or refractory or intolerant) cisplatin containing regimen for locally advanced or metastatic disease or patients who had relapsed within 12 months of cisplatin containing neoadjuvant therapy. Exclusion criteria were patients who had received prior checkpoint inhibitor targeting therapy.

Treatment regimen consisted of sEphB4-HSA 10 mg/kg IV infusion once a week plus Pembrolizumab (KEYTRUDA®) 200 mg IV infusion every 3 weeks. Tumor response was measured every 6 weeks. Baseline tissue or archival tissues are collected for biomarkers (in particular, PD-L1 IHC 22C3 PharmDx, a companion marker of Pembrolizumab/KEYTRUDA®). Independent evaluation of the response was assessed by a blinded radiologic review. PD-L1 staining was performed at a reference laboratory. All patients were eligible for toxicity assessment. Primary end point for study is OS, secondary end points are ORR and PFS. Analysis for high risk subsets includes squamous cell variant, upper urinary tract disease, liver metastasis, hemoglobin <10 mg/dl, level, and performance status over 0. Planned accrual is 60 patients. An interim analysis of 34 patients is summarized. At the time of the planned interim analysis 34 patients were consented. Three (3) of these patients were found to have been ineligible for the trial shortly after the administration of the first dose of the trial treatment. Two patients were Ineligible for CNS disease at study entry and death in one week, and one patient withdrew consent after 1 week. For the purposes of regulatory filing, these ineligible patients are included in the intent to treat analysis of the OS and PFS, but not the response rate as they were unevaluable for response.

Patient demographics can be generally summarized as follows: median age is 67 years old and 29/34 are men. 26/34 had prior cisplatin-based chemotherapy. Majority of the patients have visceral metastasis with liver involvement in 7, entry to study within 3 months in 12 cases, Hb<10 g/dL in 6. Squamous variant in 9, upper GU tract in 7. PD-L1 combined positive score of equal to or greater than 1% was present in 14 of 30 cases, tissue was not available for one patient. Laboratory developed assay for EphrinB2, the target of sEphB4-HSA was over 1% in 19 of 30 cases.

Results

With a median follow-up of 18.9 months (95% CI 15.5-27.2) using Kaplan-Meier method the median overall survival was not estimable at 21.4+ months. Median overall survival for PD-L1 positive patients was NE (95% CI 16.5-NE), and median OS in PD-L1 negative was 21.0 months (95% CI 14.9-NE). Log-rank p=0.11 (OS PD-L1 pos vs. neg). Median OS for EphrinB2 positive was 24.6 months (95% CI 14.9-NE), and EphrnB2 negative was 21.0 months (95% CI; 4.1-NE). Log-rank p=0.3 (OS EphrnB2 pos vs. neg).

PFS was 5.7 months (95% CI 2.5-14.6). Median PFS in PD-L1 positive subjects was 8.2 (95% CI 2.3-NE) and in PD-L1 negative was 4.8 months (95% CI 1.4-14.6). Log-rank p=0.13 (PFS PD-L1 pos vs. neg). Median PFS in EphrinB2 positive subjects was 14.9 months (95% CI 2.7-NE) and in EphrinB2 negative was 2.8 months (95% CI 1.3-8.2). Log rank p=0.02 (PFS EphrnB2 pos vs. neg).

ORR was 45.2% (95% CI 27-61). CR was 29.0% (9/31) (6 cases with radiographic response and 3 cases with pathologic response. Duration of response is not estimable, at 14.7+ months. PD-L1 was over 1% in 14 patients, in these patients ORR was 57.1% (8/14 patients), and CR was 35.7% (5/14 patients). Laboratory developed IHC for EphrinB2 was over 1% in 19 patients, in these patients, ORR was 63.2% (12/19 patients), and CR in 42.1% (8/19 patients). An additional patient with stable disease had resection of the one residual tumor site in the adrenal gland achieving a surgical complete remission (surgical CR or sCR) continuing at 12+ months. This patient has not been included in the response analysis.

Subset analysis shows response in upper urinary tract (5/7-71.4% ORR), squamous cell variant (4/9-44.4% ORR), visceral disease (6/16-35.2% ORR), liver metastasis (3/7-42.8% ORR), hemoglobin below 10 g/dL (2/6-33.3% ORR), and risk groups 1, 2 or 3 (4/9-44.4%, 3/7-42.8%, and 1/4-25%, respectively). All of the above data are shown in Tables 3-4.

TABLE 3

| Response Rates by Subgroup on sEphB4-HSA plus | |
| --- | --- |
| Pembrolizumab Subgroup-No. of Responders/Total No. (%) | |
| Evaluable | 31 |
| No. of responders (%) | 14/31 (45.2) |
| *Age* | |
| <65 years old | 3/12 (25.0) |
| <or = 65 years old | 11/19 (57.9) |
| Sex | |
| Male | 13/27 (48.1) |
| Female | 1/4 (25.0) |
| *ECOG Performance-Status Score* | |
| 0 | 9/21 (42.9) |
| 1 | 5/10 (50.0) |
| *Location of Primary Tumor* | |
| Upper tract | 5/7 (71.4) |
| Lower tract | 9/24 (37.5) |
| *Squamous Differentiation* | |
| Yes | 4/9 (44.4) |
| No | 10/22 (45.4) |
| *Location of Metastases* | |
| Lymph node only | 4/6 (66.7) |
| Visceral disease | 6/16 (35.2) |
| *Liver Metastases* | |
| Yes | 3/7 (42.8) |
| No | 11/24 (45.8) |
| *Hemoglobin Concentration* | |
| <10 g/dL | 2/6 (33.3) |
| or = 10 g/dL | 12/25 (48.0) |
| *No. of Risk Factors* | |
| 0 | 6/13 (46.1) |
| 1 | 4/9 (44.4) |
| 2 | 3/7 (42.8) |
| 3 or 4 | 1/4 (25.0) |
| *Context of Most Recent Therapy Received* | |
| 2$^{nd}$ line tx for met. disease | 11/20 (55.0) |
| 3rd line tx for met. disease | 2/8 (25.0) |
| 4th line tx for met. disease | 1/3 (33.3) |
| *Time Since Most Recent Chemotherapy* | |
| <3 months | 3/12 (25.0) |
| ≥3 months | 11/19 (57.9) |
| *Previous Therapy* | |
| Cemicitabin/Cisplatin | 10/25 (44.0) |
| Cemicitabin/Carbaplatin | 1/2 (50.0) |
| ddMVAC | 3/4 (75.0) |

TABLE 4

| Response Rates and Survival of sEphB4-HSA combo Study vs. Pembrolizumab Alone | | |
|---|---|---|
| | sEphB4-HSA + Pembrolizumab Study Results (N = 31) | Pembrolizumab Alone Study Results (N = 270) |
| Response | | |
| Overall Response Rate (%) | 14/31 (45.2%) (95% Cl 27, 61) | 57/270 (21.1%) (95% Cl 16.4, 26.5) |
| Complete Response Rate (%) | 9/31 (29.0%) | 19/270 (7%) |
| Progression Free Survival (Months) | | |
| Media | 5.7 (95% Cl 2.5, 14.6) | 2.1 (95% Cl 2.0, 2.2) |
| Range | 1.5-36+ | 1-22 |
| Overall Survival (Months) | | |
| Median | Not estimable (21.4+) | 10.3 (95% Cl 8, 11.8) |
| Range | 1.5-34+ | 1-22 |
| Duration of Response (Months) | | |
| Median | Not Reached (14.7+) | Not Reached (11.2+) |
| Range | 1.5-32.7+ | 1.6-15.6+ |

Figure 8:
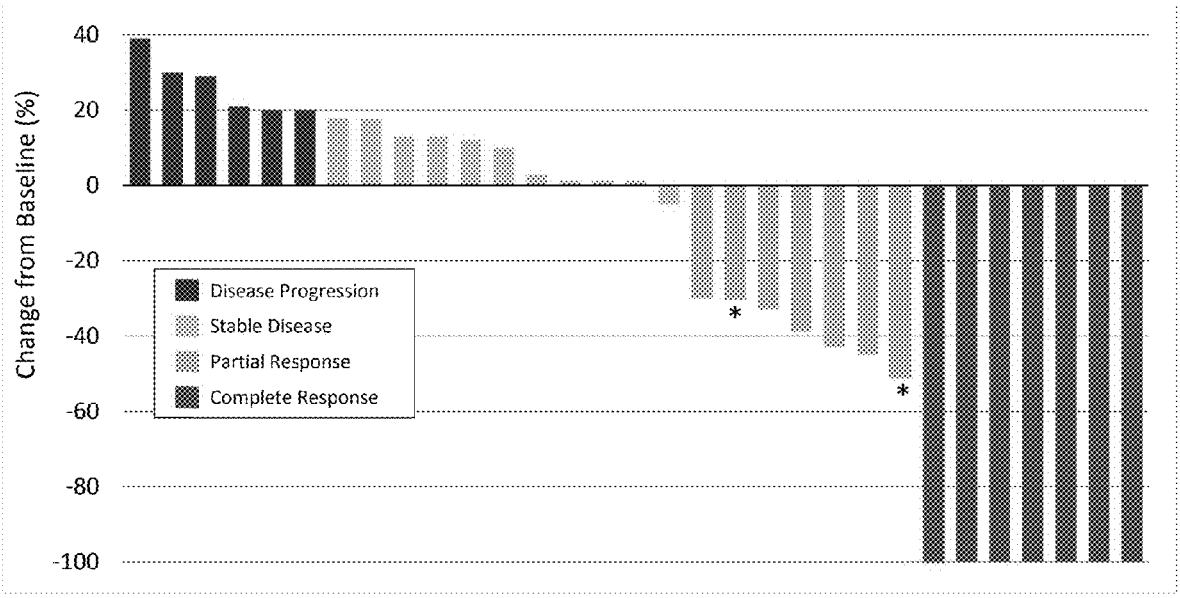
FIG. 8 depicts waterfall plot measuring the best percentage change from baseline in sum of the longest diameter for target lesions who had baseline and at least one post-baseline tumor size assessment. Tumor on biopsy and resection of only remaining sites of disease showed no evidence of tumor, thus overall response of these subjects is PR by radiology and CR by pathology.
Figure 9:
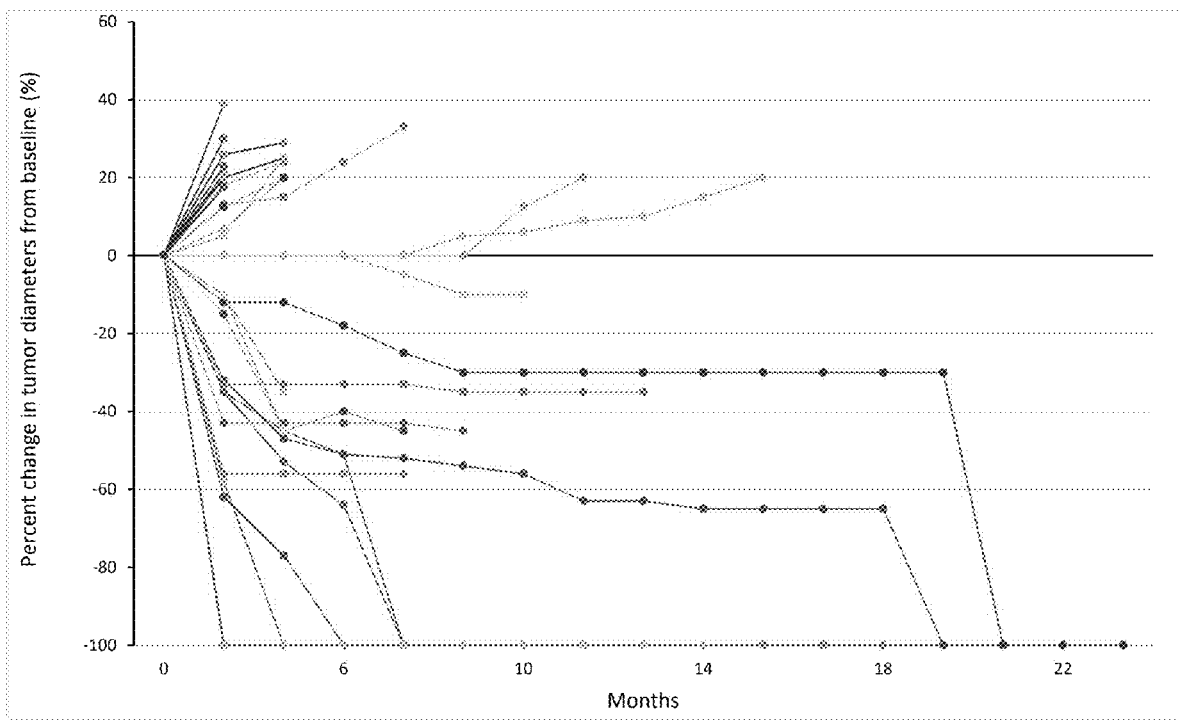
FIG. 9 depicts spider plot providing response by patient over time. Patients with disease progression (red), stable disease (yellow), partial response (light green) and complete response (dark green) are depicted.
Figure 10:
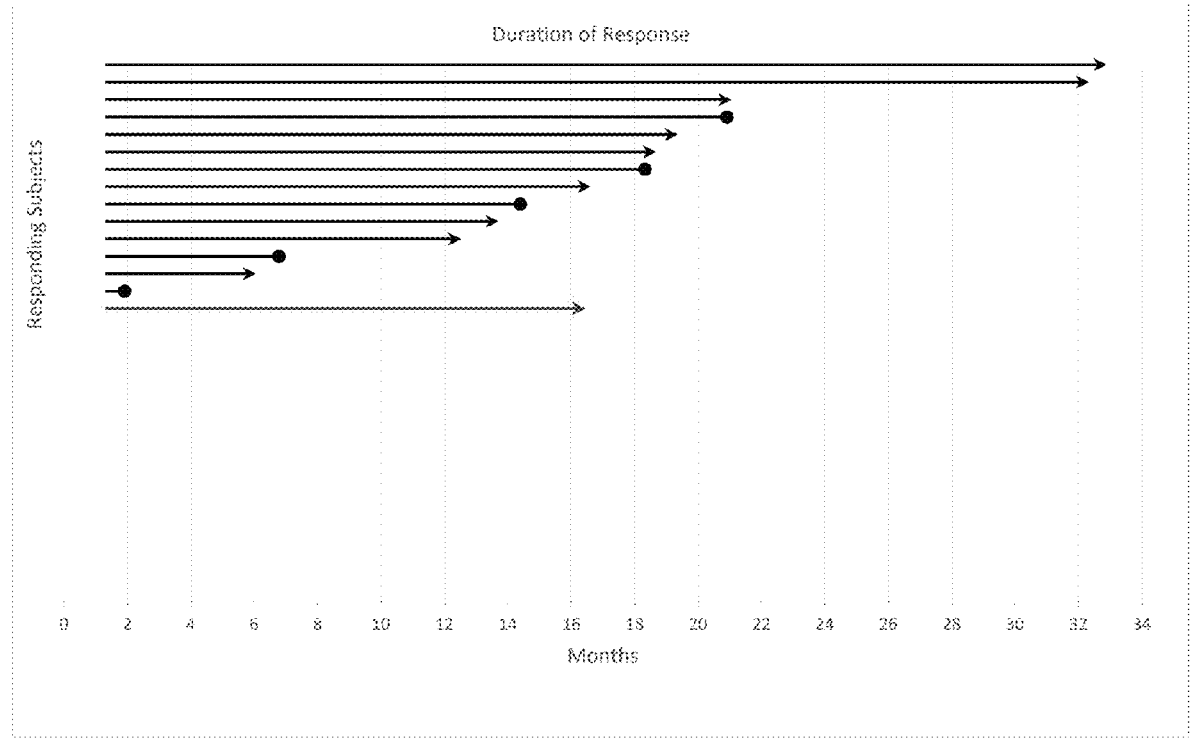
FIG. 10 depicts duration of response. Bottom arrow depicts patient with SD, had resection of residual sites of disease. Only one nodule in the adrenal gland had viable tumor. Patient remains free of disease off therapy after 12+ months.
Figure 11:
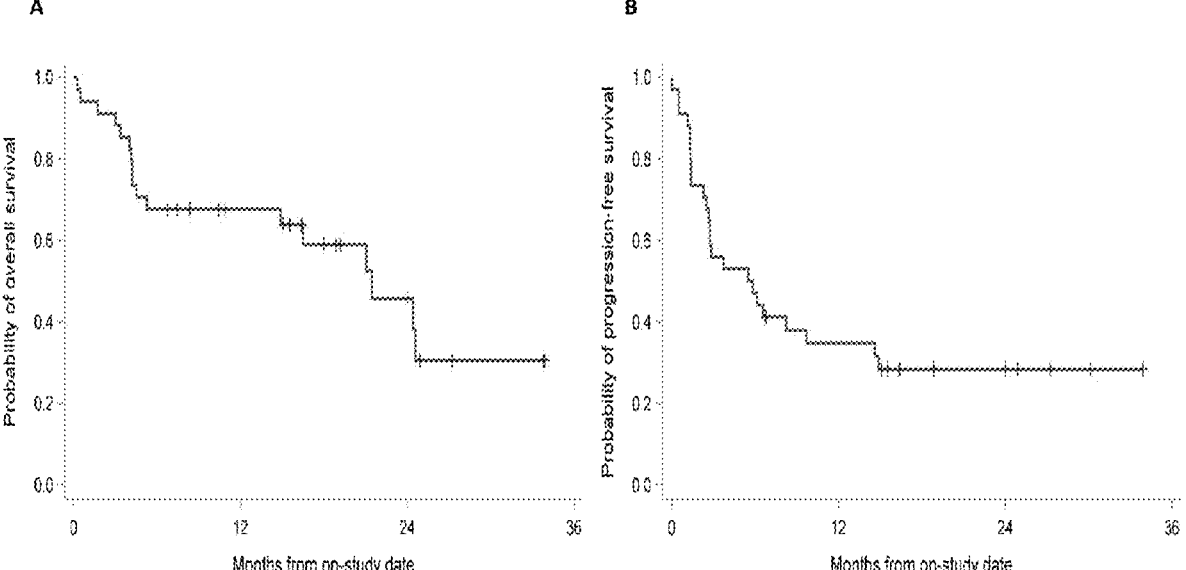
FIG. 11 depicts Kaplan-Meier plot for overall (A) and progression free survival (B). Median Progression free survival was 5.7 months (95% CI: 2.5-14.6).

Magnitude of tumor response is shown in waterfall plot (FIG. 8). Patients with partial response who either had biopsies or resection of the residual radiographic abnormalities showing no evidence of residual tumor are categorized as pathologic CR. These patients have been included in the complete remission category. These cases are also notable for the lack of tumor recurrence for long periods of time (median not estimable at 14.7+ months) while off therapy. Time to tumor regression and status of the tumor is shown in Spider Plot (FIG. 9). Complete resolution of the tumor has been observed at the first scan in some cases. Duration of response is shown in FIG. 10. Probability of median OS is 21.4 months and median PFS is 5.7 month (FIG. 11).

Figure 12:
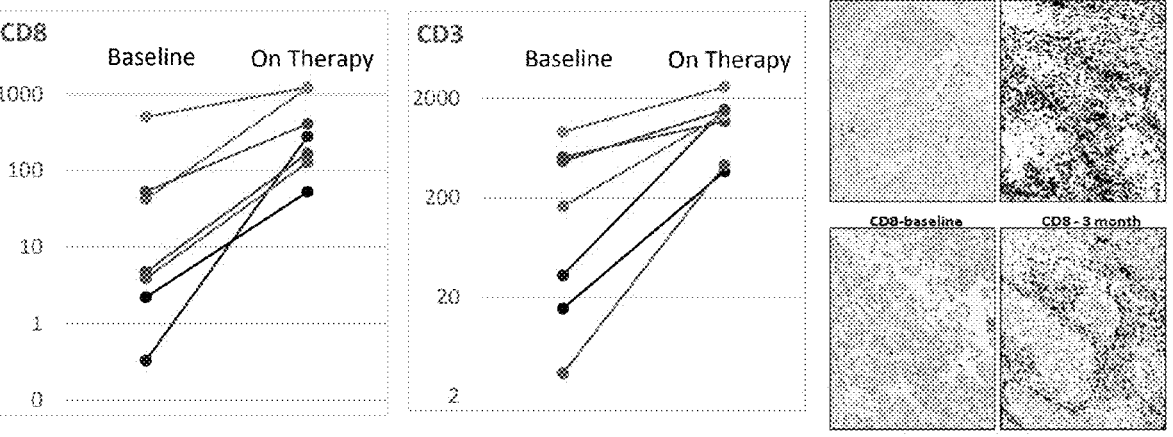
FIG. 12 depicts tumor cell infiltration with CD3 and CD8 measured in 7 patients with baseline and on therapy biopsy samples who had residual tumor on therapy. Five additional patients had no tumor at repeat biopsy (data on baseline not shown).

Tumor samples collected at baseline and second biopsy while on therapy (sEphB4-HSA plus Pembrolizumab) showed numerical increase in CD3 and CD8 cells with combination therapy shown below. Specifically, patients with low or no resident T cells at baseline also show an increase in CD3 and CD8 cells with therapy especially in tumors with baseline EphrinB2 expression using laboratory developed assay (FIG. 12). Tumor cell infiltration with CD3 and CD8 was measured in 7 patients with baseline and on therapy biopsy samples who had residual tumor on therapy. Five additional patients had no tumor at repeat biopsy (data on baseline not shown).

PD-L1 is established as frontline treatment of urothelial cancer with immune check point inhibitors. There is numerical difference in relapsed/refractory urothelial cancer treated with immune check point inhibitors, but not statistically significant. PD-L1 expression and response to combination of sEphB4-HSA plus Pembrolizumab was assessed in 30 of the 31 cases Table 5.

TABLE 5

| PD-L1 Expression and Overall Response | | |
|---|---|---|
| Population | ORR (%) PD-L1 Positive (N = 14) | ORR (%) PD-L1 Negative (N = 16) |
| Overall (N = 30) | 8/14 (57.1) | 6/16 (37.5) |
| EphrinB2 Positive (N = 19) | 7/8 (87.5) | 6/11 (54.5) |
| EphrinB2 Negative (N = 11) | 1/6 (16.7) | 1/5 (20.0) |

EphrinB2 is the target for sEphB4-HSA. EphrinB2 expression and correlation with therapy is thus a potential biomarker. EphrinB2 immunohistochemical staining in bladder cancer was done with a laboratory-based assay, using a commercially available monoclonal antibody. Staining has been done using Leica platform in a CLIA certified laboratory. All stained tissues were reviewed by single pathologist blinded to time of tissue acquisition (baseline or on therapy), and patient treatment outcome. Specificity of the antibody was done using isogenic cell lines lacking EphrinB2 expression (Chinese hamster ovary or CHO cells) or engineered to express human EphrinB2 or closely related proteins (EphrinB1 or EphrinB3). EphrinB2 expression and response to combination regimen are shown in the Table 6 below.

TABLE 6

| EphrinB2 Expression. Patient Response Rate: Responders/Total (%) | | |
|---|---|---|
| Population | ORR (%) EphrinB2 Positive (N = 19) | ORR (%) EphrinB2 Negative (N = 11) |
| Overall (N = 30) | 12/19 (63.2) | 2/11 (18.2) |
| PDL-1 Positive (N = 14) | 7/8 (87.5) | 1/6 (16.7) |
| PDL-1 Negative (N = 16) | 6/11 (54.5) | 1/5 (20.0) |

Combination of sEphB4-HSA and Pembrolizumab is well tolerated. First six patients were evaluated for safety of the combination at full doses. Combination was well tolerated with no new toxicities observed from combination therapy. sEphB4-HSA single agent safety study showed frequent occurrence of hypertension. Hypertension was noted in the combination of sEphB4-HSA plus Pembrolizumab. Pembrolizumab-related toxicities were also observed in this combination study. No new or unexpected toxicities were observed. Long term use of combination of sEphB4-HSA plus Pembrolizumab did not lead to new and unexpected toxicities. Toxicity summary is shown below in Table 7.

TABLE 7

| | sEphB4-HSA + Pembrolizumab (N = 31) | | Pembrolizumab (N = 266). NEJM 2017; 376:1015 | |
| Treatment-Related Event | Any Grade | Grade 3, 4 or 5 | Any Grade | Grade 3, 4 or 5 |
|---|---|---|---|---|
| Any Event | | | | |
| Event leading to discontinuation of treatment | 1 (3.2%) | 1 (3.2%) grade 3 | 162 (60.9%) | 40 (15.0%) |
| Event leading to death | 1 (3.2%) | 1 (3.2%) grade 3 | 15 (5.6%) | 12 (4.5%) |
| Event Occurring in ≥10% of Patients | | | | |
| Pruritus | 7 (22.5%) | 0 | 52 (19.5%) | 0 |
| Fatigue | 11 (35.5%) | 0 | 37 (13.9) | 3 (1.1%) |
| Nausea | 3 (9.7%) | 0 | 29 (10.9%) | 1 (0.4%) |
| Diarrhea | 3 (9.7%) | 0 | 24 (9.0%) | 3 (1.1%) |
| Decreased Appetite | 0 | 0 | 23 (8.6%) | 6 (2.3%) |
| Asthenia | 2 (6.5%) | 1 (3.2%) grade 3 | 15 (5.6%) | 1 (0.4%) |
| Anemia | 2 (6.5%) | 1 (3.2%) grade 3 | 9 (3.4%) | 2 (0.8%) |
| Constipation | 2 (6.5%) | 0 | 6 (2.3%) | 0 |
| Peripheral Sensory Neuropathy | 2 (6.5%) | 0 | 2 (0.8%) | 0 |
| Neutrophil Count Decrease | 0 | 0 | 1 (0.4%) | 1 (0.4%) |
| Peripheral Neuropathy | 0 | 0 | 1 (0.4%) | 0 |
| Neutropenia | 0 | 0 | 0 | 0 |
| Alopecia | 0 | 0 | 0 | 0 |
| Events of Interest | | | | |
| Any Event | 6 (19.4%) | 0 | 45 (16.9%) | 12 (4.5%) |
| Hypo | 2 (6.5%) | 0 | 17 (6.4%) | 0 |
| Hyperthyroidism | 0 | 0 | 10 (3.8%) | 0 |
| Pneumonitis | 1 (3.2%) | 0 | 11 (4.1%) | 6 (2.3%) |
| Colitis | 0 | 0 | 6 (2.3%) | 3 (1.1%) |
| Infusion Reaction | Chill-3 (9.7%)/ Fever 1 (3.2%) | 0 | 2 (0.8%) | 0 |
| Nephritis | 0 | 0 | 2 (0.8%) | 2 (0.8%) |
| Severe Skin Rash | 0 | 0 | 2 (0.8%) | 1 (0.4%) |
| Nephritis | 0 | 0 | 0 | 0 |
| Thyroiditis | 0 | 0 | 2 (0.8%) | 0 |
| Adrenal Insufficiency | 0 | 0 | 1 (0.4%) | 1 (0.4%) |
| Myositis | 0 | 1 grade 5 | 0 | 0 |
| Hypertension | 9 (29) | 12 (38.7) grade 3 | 0 | 0 |

SUMMARY vsEphB4-HSA combination with Pembrolizumab shows median OS of 21.4+ months, PFS of 5.7 months and ORR of 45%, and CR of 29%. High risk variants of urothelial cancer showed response including squamous cell variants in 5 of 9 patients (55.6%), and upper tract disease in 5 of 8 patients (62.5%). Patients with Bellmunt risk group 2 in 3 of 7 (42.8%) and risk group 3/4 in 1 of 5 (20%). For historical comparison, Pembrolizumab has been studied in the same patient population. Pembrolizumab shows an ORR of 21.1% (95% CI 16.4-26.5), progression free survival of 2.1 months (95% CI, 2.0 to 2.2) and overall survival of 10.3 months (95% CI 8.0 to 11.8). Four additional PD-1 (Nivolimab) or PD-L1 (Atezulimumab, Durvalumab, Avelumab) antibodies are approved by the FDA for this patient population. Median overall survival for these agents is as follows: Nivolimab—8.7 months, Atezolimumab—7.9 months, Durvalumab—18.2 months, and Avelumab—6.5 months. PFS for all five antibodies is 2.1 months or less. ORR is 21.1% or less with CR of 7% or less.

Combination of sEphB4-HSA plus Pembrolizumab has substantial efficacy and durability in relapsed/refractory urothelial cancer patients who have an expected median survival of less than one year. Patients achieving CR remain free of cancer off therapy in the majority of cases. Combination of sEphB4-HSA plus Pembrolizumab has substantial benefit in all subgroups including patients with variant histology, upper urinary tract, low hemoglobin, performance status of 2, 3 and 4, liver metastasis, Bellmunt poor risk subgroups, and PD-L1 negative patients.

Treatment is well tolerated when combined with PD-1 antibody, without apparent overlapping toxicity, and the treatment can be administered for prolonged periods of time. A laboratory developed assay for EphrinB2, the target for sEphB4-HSA, shows higher ORR of 68.4% (13/19 patients) in EphrinB2 positive tumor. Patients positive for both EphrinB2 and PD-L1 have ORR rate of 87.5% (7/8 patients). Patients negative for PD-L1 have ORR of 37.5% (6/16 patients).

The activity of combination of sEphB4-HSA combined with PD-1 antibody appears to occur by the complementary functions where sEphB4-HSA promotes migration of T cells into the tumor while PD-1 antibody activates newly recruited and resident immune cells to achieve durable response.

Example 5

Figure 13:
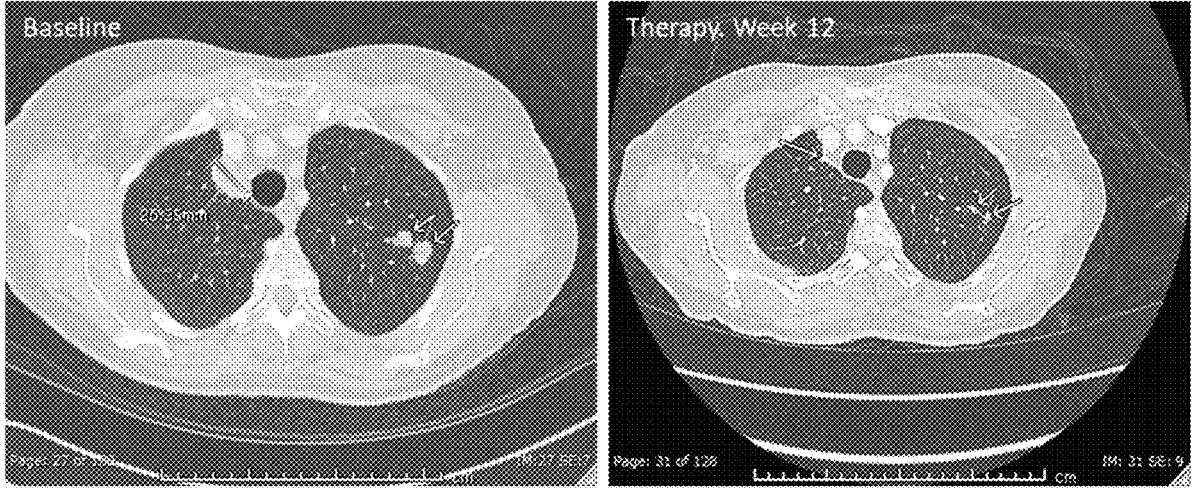
FIG. 13 depicts a 63-year old woman with widely metastatic bladder cancer was placed on sEphB4-HSA+ Pembrolizumab. Scan above at week 12 shows over 90% regression of lung metastasis.

In this example, a 63-year old woman with locally advanced bladder cancer was treated with neoadjuvant gemcitabine cisplatin chemotherapy and taken to radical cystectomy. However, she recurred shortly after surgery with rapidly progressive disease at multiple sites including numerous large bilateral lung disease. She was placed on sEphB4-HSA plus pembrolizumab therapy. She had deep response within 6 weeks of therapy; and continues on therapy. Scan taken at week 12 (FIG. 13) depicts a 90% regression of lung metastasis.

Figure 14:
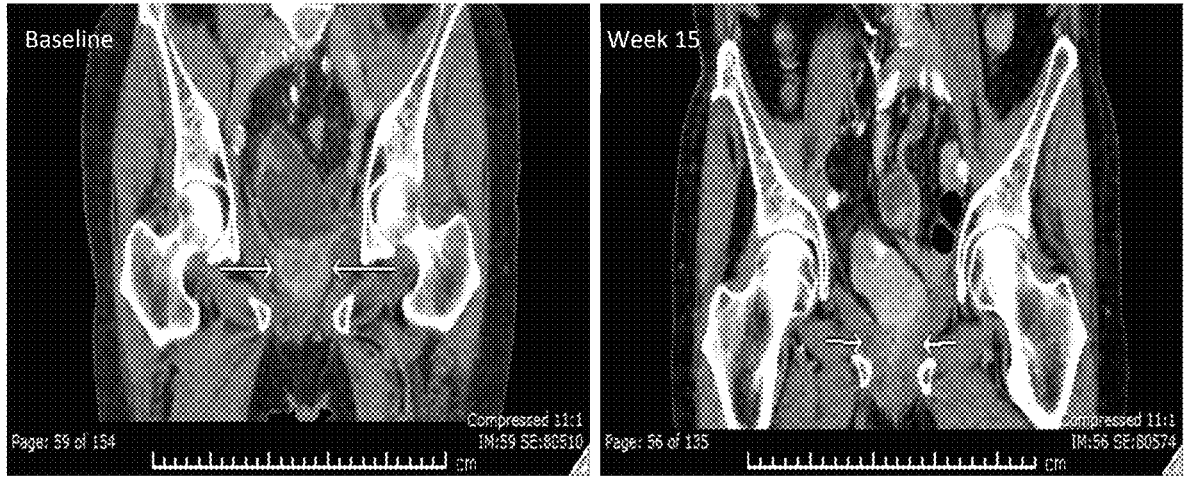
FIG. 14 depicts a 79-year old man male with neo-bladder. Large mass resolved completely at week 15 on therapy; patient remains on therapy.

A 79-year old man male with neo-bladder, with extensive local recurrence after neoadjuvant gemcitabine and cisplatin chemotherapy followed by radical cystectomy. He was placed on sEphB4-HSA+Pembrolizumab. Large mass resolved completely at week 15 on therapy; and continues on therapy past week 15. Scan taken at week 15 (FIG. 14).

Example 6

In this example, we found that EphB4-Ephrin-B2 inhibition alone or in combination with radiation (RT) reduces intratumoral regulatory T cells (Tregs) and increases activation of both CD8+ and CD4+Foxp3– T cells compared to the control group in an orthotopic head and neck squamous cell carcinoma (HNSCC) model. We also compared the effect of EphB4-ephrin-B2 inhibition combined with RT to the anti-PDL1 and RT combination and observed similar tumor growth suppression particularly at early time-points. Our data in a patient-derived xenograft model shows reduction of tumor-associated M2 macrophages, favoring polarization towards an anti-tumoral M1 phenotype following EphB4-ephrin-B2 inhibition with RT. In vitro, EphB4 signaling inhibition decreases Ki67-expressing Tregs, and Treg activation compared to the control group. Overall, our study represents the first report implicating the role of EphB4-ephrin-B2 in tumor immune response and our findings suggest that EphB4-ephrin-B2 inhibition combined with RT represents a potential alternative for HNSCC patients and could be particularly beneficial for patients who are ineligible to receive or cannot tolerate anti-PDL1 therapy. Our study presents EphB4-ephrin-B2 inhibition as a novel alternative to anti-PDL1 therapeutics that can be used in combination with radiation to induce an effective anti-tumor immune response in HNSCC patients.

To investigate the contribution of the tumor immune microenvironment to tumor growth retardation due to EphB4-ephrin-B2 inhibition, CyTOF analysis was conducted on Ly2 tumors on days 14 to 18 after administration of the TNYL-RAW-Fc plasmid (see Materials and Methods below) or pcDNA3 control plasmid. Our data show significant changes in tumor-infiltrating immune cells following TNYL-RAW-Fc treatment. In particular, CD8+ T cells in the tumors showed a 1.2-fold increase (p=0.03) following TNYL-RAW-Fc treatment compared to pcDNA3 control. The percentage of CD4+ T cells, however, remained unchanged. The Treg cells (CD4+ T cells that are also positive for the Foxp3 marker) constitute an important immunosuppressive population in the TME and were dramatically reduced by ~3 fold (p=0.009) in the EphB4-ephrin-B2 inhibited group. Importantly, the CD8+ Teff cell/Treg ratio that is an indicator of enhanced therapeutic response, also significantly increased (p=0.02) following EphB4-ephrin-B2 inhibition. Additionally, the activation status of both conventional CD4+Foxp3– T cells and CD8+ T cells, assessed based on ICOS (Inducible T-cell COStimulator) expression, showed a ~2.8-fold increase (p=0.0002; p=0.009) following EphB4-ephrin-B2 inhibition.

In addition to the changes observed in T cells, we also observed changes in the macrophage population (F4/80+ cells, gated on CD11b+ cells. There was a 1.9-fold decline (p=0.04) in the F4/80+ macrophages in the TNYL-RAW-Fc treated group. Specifically, we noted a 1.4-fold decline (p=0.01) in the pro-tumorigenic M2 macrophages (Arg1+ F4/80+ cells) and a 16-fold increase (p<0.0001) in M1 macrophages (F4/80+iNOS+) following TNYL-RAW-Fc treatment. No significant differences were detected in intratumoral CD11b+Ly6C+ monocytes or CD11b+Ly6G+ neutrophils. We also observed a 1.7-fold upregulation (p=0.01) in the CD110+ dendritic cell population following EphB4-ephrin-B2 blockade.

To understand the mechanisms by which EphB4-ephrin-B2 interaction affects T cell numbers and function in HNSCC tumors, we conducted in vitro analyses of CD4+ T cells isolated from the spleens of tumor-bearing mice and treated for 72 hours with recombinant ephrin-B2-Fc. We selected recombinant ephrin-B2-Fc protein for in vitro studies because at high concentrations (20 µg/ml) it has been reported to inhibit certain EphB4 downstream signals. We observed lower levels of tyrosine phosphorylated EphB4 in CD4+ T cells treated with 20 µg/ml ephrin-B2-Fc than in CD4+ T cells treated with Fc control. To confirm these results, we also treated the CD4+ T cells with PEGylated form of TNYL-RAW peptide EphB4 antagonist, also known to block EphB4-ephrin-B2 interaction and observed similar effect.

We examined the effect of ephrin-B2-Fc treatment on Ki67 (a surrogate marker of proliferation) expressing Tregs using flow cytometry and observed that ephrin-B2-Fc at 20 µg/ml concentration decreased Ki67 expressing Tregs by 1.7-fold (p=0.02) compared to the Fc control treatment. The percentage of total CD4+ T cells remained unchanged between control and ephrin-B2-Fc treated groups.

Tregs also constitutively express high levels of IL-2Ra and depend on IL-2 for proliferation, survival and proper functioning. Since we observed decreased Ki67-expressing Tregs following a high dose of ephrin-B2-Fc, we investigated if this may be mediated by reduced secretion of cytokines such as IL-2. Our data indeed show a decrease in the secreted levels of IL-2 (p=0.07) as well as of TGF-β. (p=0.009), a key regulator of Treg function, in the conditioned media of Treg cells treated with 20 µg/ml ephrin-B2-Fc. In addition, decreased levels of pro-survival markers such as p-AKT, and Bcl-XL were observed in T cell lysates by western blotting after 24 hours treatment with the high concentration of ephrin-B2-Fc compared to the control-Fc. The levels of cleaved caspase-3, on the other hand, increased following treatment with 20 µg/ml ephrin-B2-Fc compared to the control-Fc.

We evaluated the efficacy of combining EphB4-ephrin-B2 inhibitor, TNYL-RAW-Fc, with RT to suppress tumor growth by modulating the tumor immune microenvironment and mitigating the pro-tumorigenic effects of EphB4-ephrin-B2 signaling in the Ly2 orthotopic model. We also compared the in vivo efficacy of combined EphB4-ephrin-B2 inhibition and RT with that of combined immune checkpoint inhibitor anti-PDL1 and RT. Our data show that radiation alone (RT+IgG+pcDNA3) reduced tumor growth by 2.2-fold (p=0.0003) compared to the IgG+pcDNA3 control group. However, when TNYL-RAW-Fc was used in combination with RT, the combination group resulted in a 4.4-fold reduction compared to TNYL-RAW-Fc alone (p=0.0003). Importantly, when EphB4-ephrin-B2 inhibition was combined with RT, a similar anti-tumor response was generated as anti-PDL1 combined with RT at day 20 post-tumor implantation. Triple combination with anti-PDL1+RT and TNYL-RAW-Fc did not add additional synergy. Monitoring tumor growth over extended period of time showed enhanced tumor growth suppression in the RT+IgG+TNYL combination group compared to RT+IgG+pcDNA3 in Ly2 tumors. We also evaluated the efficacy of combining TNYL-RAW-Fc inhibitor with RT in another aggressive HNSCC tumor model, Moc2 and it showed similar tumor growth suppression in the combination groups compared to single-agent RT alone. Treating Moc2 tumors with RT resulted in a significant 1.59-fold reduction (p<0.0001) in tumor growth compared to the control pcDNA3 group. When TNYL-RAW-Fc inhibitor was combined with RT, it decreased tumor growth by 1.36-fold (p<0.005). The irradiated groups when combined with either TNYL-RAW-Fc or anti-PDL1 resulted in similar level of tumor growth suppression compared to RT alone at day 17 and day 21 post-tumor implantation. Similar to the Ly2 model, combining TNYL-RAW-Fc inhibitor with anti-PDL1+RT failed to show any additional benefit.

To understand the contribution of EphB4-ephrin-B2 inhibition to immune modulation in the presence of RT, we analyzed Ly2 tumors harvested from the control and TNYL-RAW-Fc groups with and without RT by flow cytometry. Our data demonstrated that in the absence of RT, EphB4-ephrin-B2 inhibition increased CD8+ T cell population without affecting the CD4+ T cell subset. Exposing Ly2 tumors to 10 Gy dose of RT resulted in a significant enhancement of both CD8+ T cells and CD4+ T cells at day 3 post-RT. EphB4-ephrin-B2 inhibition with RT did not affect these T cell populations compared to RT alone. We observed a 1.6-fold decline in the Treg population with RT treatment compared to the control group at day 3 post-RT (p=0.009). Addition of TNYL-RAW-Fc to RT resulted in a further decline (~2.7-fold total) in the tumor-infiltrating Tregs compared to both of the single agents. The CD8+ T cell to Treg ratio was also significantly increased in the combination treatment compared to control or TNYL-RAW-Fc treatment. To examine the effect of EphB4-ephrin-B2 inhibition with RT on T-cell function, we evaluated the percentage of activated CD8 T cells (CD8+IFNγ+) and activated conventional CD4 T cells (CD4+Foxp3-IFNγ+). We observed an increase in the percentage of both in the combination group (2.2-2.4-fold) compared to TNYL-RAW-Fc alone. In addition, inhibiting EphB4-ephrin-B2 interaction with RT also resulted in a significant increase in CD4+Foxp3-IFNγ+ cells (2.2-fold) (p=0.04) compared to RT alone. Increased levels of secreted IP-10/CXCL10, a potent chemokine that attracts functional cytotoxic T cells, was induced by TNYL-RAW-Fc or RT treatment, and further increased by the combination of both treatments compared to RT. Finally, a 1.4 and 1.8-fold decrease in circulating TGF-β, an output of Tregs' immunosuppressive action, was observed with the TNYL-RAW-Fc and RT treatment, respectively, compared to the control group. Combining TNYL-RAW-Fc with RT further potentiated the decrease in TGF-β levels (p=0.02 compared to RT).

To determine whether the decrease in TAMs is a direct consequence of the changes in Tregs, which are known to promote monocyte differentiation to macrophages, we tested the effect of EphB4-ephrin-B2 inhibition in nude mice, a T cell independent model. We used HNSCC PDX tumor models known to preserve the tumor environment and mimic human cancers. We have previously shown a significant decrease in tumor growth following EphB4-ephrin-B2 inhibition using sEphB4-HSA in combination with radiation only or radiation and the EGFR inhibitor cetuximab. sEphB4-HSA is a soluble protein that inhibits the interaction between EphB4 and ephrin-B2 by binding to ephrin-B2 (while TNYL-RAW inhibits the interaction by binding to EphB4). We measured TAM infiltration by using T2 weighted-MRI with iron oxide (SPIO) accumulation in a HNSCC PDX tumor model. We observed that while RT by itself considerably increases SPIO uptake as represented by decreased signal intensity, inhibiting EphB4-ephrin-B2 interaction with sEphB4-HSA reversed this effect of RT (p<0.05).

These imaging data were further corroborated by IF staining using CUHNO13 tumors harvested from control and experimental groups. This demonstrated that inhibition of EphB4-EphrinB2 with sEphB4-HSA in combination with RT significantly decreases the percentage of TAMs, as determined by the reduction in the staining for the pan-macrophage markers CD107b+ and F4/80+ compared to either treatment alone. We also observed a decrease in the staining for CD163+ M2 macrophages and an increase in the staining for Gpr18+ M1 macrophages in CUHNO13 tumors, suggesting that EphB4-ephrin-B2 inhibition and RT shift the polarization of macrophages from the pro-tumor M2 phenotype to the anti-tumor M1 phenotype. This is also evident in the increased ratio of M1 to M2 markers (Gpr18:CD163), which is potentiated in the combination group. Finally, analysis of circulating cytokine/chemokine profiles demonstrates that combining sEphB4-HSA with RT significantly decreases the levels of macrophage colony-stimulating factor (M-CSF), a key differentiation factor that mediates M2 polarization, compared to the single agent treatments. This is accompanied by a marked increase in the levels of both GM-CSF and IFNγ, particularly in the combination treatment group as compared to either sEphB4-HSA alone or RT alone. Both GM-CSF and IFNγ are known to favor M1 polarization. Thus, taken together, our data indicate that combined EphB4-ephrin-B2 inhibition and RT induce an anti-tumor immune response by affecting macrophage polarization.

In light of our data showing that EphB4-ephrin-B2 inhibition favors a polarization towards an M1 phenotype, we performed TOGA and CIBERSORT analysis to examine the significance of such polarization on the survival of HNSCC patients. Our analysis revealed for the first time that a significant correlation exists between lower M1/M2 ratio and poor overall survival as well as disease-free survival. The analysis was based on a cut-off M1/M2 ratio of 0.5. When the M1/M2 ratio is <0.5, patients have poor overall survival rates compared to patients with M1/M2 ratio >0.5. The median survival for patients with M1/M2 ratio >0.5 was 65.8 months compared to 32.8 months (p=0.0170) for patients with M1/M2 ratio <0.5. Furthermore, the median time to disease progression in patient cohort with M1/M2 ratio >0.5 was 76.2 months compared to 53.1 months (p=0.0111) for patients with <0.5 M1/M2 ratio.

Materials and Methods

Cell Culture and Reagents

The murine Moc2 cell line was obtained from Dr. Ravindra Uppaluri (Dana-Farber Cancer Institute, MA) and the Ly2 cell line was obtained from Dr. Nadarajah Vigneswaran (University of Texas Health Science Center, TX). Ly2 cells were cultured in DMEM-F12 and Moc2 cells in IMDM medium. The medium was supplemented with 10% FBS and 1% primocin and cells were cultured at 37° C. in a 5% $CO_2$ incubator. The soluble EphB4 extracellular domain fused to human serum albumin (sEphB4-HSA) was used to inhibit EphB4-ephrin-B2 interaction in a PDX immunocompromised mouse model. The sEphB4-HSA protein was provided by Dr. Parkash Gill (University of Southern California, CA; Vasgene Therapeutics, Inc.). For immunocompetent mouse models, a plasmid encoding the 15 amino acids long TNYL-RAW peptide fused with the Fc portion of human IgG1 (TNYL-RAW-Fc, an EphB4 antagonist) was used to block EphB4-ephrin-B2 signaling. pcDNA3 plasmid was used as a control. The plasmids were obtained from Dr. Elena Pasquale's lab (Sanford Burnham Prebys Medical Discovery Institute, CA). The PEGylated form of TNYL-RAW peptide was obtained from Anaspec (Fremont, CA) for in vitro studies involving T cells.

In Vivo Models

All mice were handled and euthanized in accordance with the ethics guidelines and conditions set and overseen by the University of Colorado, Anschutz Medical Campus Animal Care and Use Committee. For immunocompromised mouse model studies, female athymic nude mice (5-6 weeks old, n=5-7 per group) were purchased from Envigo (Indianapolis, IN, USA). The HNSCC PDX tumors CUHNO13 and CUHNO04 (F8-F16 generation) were obtained from Dr. Antonio Jimeno's lab (University of Colorado, Anschutz Medical Campus, Aurora, CO).

Tumor implantations were performed as described earlier (25). When tumor volumes reached approximately 50-150 $mm^3$, mice were randomized into four groups (1) PBS, (2) sEphB4-HSA, (3) PBS+RT, and (4) sEphB4-HSA+RT. Mice were either injected with PBS or with a 20 mg/kg dose of sEphB4-HSA (three times/week) and/or subjected to RT (5 Gy/fraction×4 fractions) as described earlier.

For iron oxide imaging studies, superparamagnetic iron oxide (SPIO) nanoparticles were generated. The detailed protocol for magnetic resonance (MR) imaging as reported by Serkova et al. was followed. MR imaging was performed before treatment and 96 hours after the last dose of RT. Final images were processed with ParaVi-sion software (Bruker Biospin).

For immunocompetent mouse model studies, 5-6 week-old female BALB/c mice (Charles River Laboratories, Wilmington, MA) or C57BL/6 mice (Jackson Laboratories, Bar Harbor, ME) were used. Tumor cell inoculation was performed as described earlier. Seven to eight mice were implanted per experimental or control group. Mice were randomized at day 4-5 post-tumor inoculation (tumor volume ~50 $mm^3$) to receive either pcDNA3 control plasmid or TNYL-RAW-Fc plasmid via hydrodynamic injection as described earlier. Briefly, 20 µg of plasmid DNA was resuspended in ~2 ml of PBS and injected into the tail-vein in less than 6 seconds. Tumor sizes were measured biweekly with digital calipers and tumor volumes were estimated using the formula [(smaller diameter)$^2$× longest diameter/2]. For combination therapy studies, mice were randomized into IgG+ pcDNA3 control, IgG+TNYL-RAW-Fc, anti-PDL1+TNYL-RAW-Fc, RT+IgG+pcDNA3, RT+IgG+TNYL-RAW-Fc, RT+anti-PDL1+pcDNA3, and RT+anti-PDL1+TNYL-RAW-Fc. IgG2b control (referred as IgG; BioXcell, NH) and anti-PDL1 (BioXcell, NH) were administered intraperitoneally at a dose of 10 mg/kg twice a week throughout the course of experiment. pcDNA3 and TNYL-RAW-Fc were administered as described above. RT was administered at a single dose of 10 Gy as described earlier. Plasmid DNA treatment was initiated on day 5 after tumor inoculation and administered as a single dose. IgG2b or anti-PDL1 was initiated in combination with RT on day 7-9 after tumor inoculation and continued throughout the course of experiment. Mice were euthanized according to the guidelines set by the Institutional Animal Care and Use Committee (IACUC). Tumor tissue was harvested at the time of sacrifice and either fixed in 10% neutral buffered formalin or flash-frozen for further analysis.

Immune Cell Depletion Studies

CD8 T cell depletion was performed using an anti-CD8 antibody (Clone 53-6.7, 10 mg/kg, i.p. BioXcell, NH) and the corresponding rat IgG1 isotype was used as a control. The antibodies were administered 1 week prior to tumor implantation and were continued once a week for 3 weeks after tumor implantation. TNYL-RAW-Fc or pcDNA3 treatment (20 µg/2 ml PBS; hydrodynamic tail-vein injection) was performed on day 4 after tumor implantation because of the aggressive nature of tumor models used in this study. Flow cytometry was performed to confirm systemic depletion of CD8+ T cells by using an anti-CD8 antibody clone that do not compete with clone 53-6.7 used for depletion experiment.

Flow Cytometry

Tumors and spleens were processed into single-cell suspensions for flow cytometric analysis as described earlier and 1-2×10$^6$ live cells were plated in a 96-well plate followed by blocking with anti-CD16/32 antibody. For analysis of immune cells, cytokines, and phospho-STAT3 marker, the following conjugated antibodies were used: AlexaFluor700-CD45 (1:50, Clone 30-F11, cat #56-0451-82, eBioscience), BUV737-CD11b (1:100, Clone M1/70, cat #564443, BD Biosciences), FITC-F4/80 (1:100, Clone BM8, cat #123108, Biolegend), DyLight350-CD3 (1:100, Clone 145-2C11, Novus Biologicals), eFluor450-CD4 (1:100, Clone RM4-5, cat #48-0042-82, eBioscience), APC-eFluor780-CD8 (1:100, Clone 53-6.7, cat #47-0081-82, eBioscience), PECyanine7-IFNγ (1:20, Clone XMG1.2, cat #25-7311-82, eBioscience), Ki67-BV605 (1:50, Clone 16A8, cat #652413, eBioscience), p-STAT3-PE (1:5, clone 49; p 727, cat #558557, eBioscience).

For cytokine release experiments, single cell suspensions were plated in 6-well plates in the presence of monensin (to block cytokine release) and a cell activation cocktail with Brefeldin to stimulate cytokine production at 37° C. for 3.5-4 hours. After washes with FA3 buffer (PBS, 10 mM HEPES, 2 mM EDTA, 1% FBS), the cells were stained with surface marker antibodies diluted in FA3 buffer/Fc block (1:100 dilution) at room temperature for 30 min. After subsequent washes, the cells were resuspended in 100 µl of Cytofix/CytoperM™ solution (BD Biosciences) for 20 min at 4° C. Following incubation, cells were washed with 1× Perm/Wash™ solution (BD Biosciences) and stained with anti-cytokine antibodies at 4° C. for 30 min. Cell pellets were resuspended in FA3 buffer and samples were run on the YETI cell analyzer. To detect STAT3 phosphorylation (p-STAT3) and Ki67 expression in cultured T cells by flow cytometry, single cell suspensions treated with pre-clustered control Fc, 20 µg/ml ephrin-B2-Fc, or PEGylated TNYL-RAW (4.5 µg/ml) following treatment with stimulating dose of ephrin-B2-Fc (2.5 µg/ml) for 24-48 h were stained with immune cell surface markers. This was followed by incubation in 1× lyse/fix buffer (BD Biosciences) at 37° C. for 30 min. Pre-clustering was performed by incubating Fc proteins with hIgG in the ratio of 1:3 at 4° C. for 30 min in an orbital shaker.

Following washing with PBS, samples were resuspended in cold perm III buffer (BD Biosciences), incubated on ice for 15 min, and stained with p-STAT3 or Ki67 antibodies for 30 min at room temperature. After washes with FA3 buffer, the samples were run on the YETI cell analyzer. Various controls such as beads only, samples stained with a single antibody, isotype controls, and fluorescence minus-one (FMO) controls were also included. Live cells were gated using Aqua/vi live/dead stain. Stained cells were run on the YETI Cell Analyzer at the University of Colorado Denver Cancer Flow Cytometry Core. Data was analyzed using Kaluza analysis software.

RNA Extraction and qPCR Analysis

Tregs and monocytes were harvested from Ly2 tumors using isolation kits (Stemcell Technologies). Monocytes were treated with IL-4 (25 ng/ml) to allow differentiation into M2 macrophages. Total RNA was collected from Tregs and macrophages using RNeasy mini prep kits (Qiagen). cDNA was prepared from 5 μg of RNA sample in a reverse transcription reaction using Maxima First Strand cDNA Synthesis Kit (Thermo Scientific). Aliquots (2 μL) of a 1:2 dilution of the reverse transcription reactions were subjected to quantitative real-time PCR (RT-PCR) in 10 μL reactions with SYBR Select Master Mix (Thermo Fisher Scientific) with the following primers using a iQ real time-PCR detection system (BioRad). GAPDH mRNA levels were analyzed as a housekeeping gene for normalization purposes. Similar RNA extraction and qPCR protocol was used to detect mRNA levels of EPHB4 and EFNB2 in Ly2 tumors in the absence and presence of 10 Gy dose of RT.

Mass Cytometry (CyTOF)

For mass cytometry experiments, tumors were harvested and digested as described above in the flow cytometry section. Single cell suspensions were washed with PBS and stained with heavy metal tagged antibodies according to manufacturer instructions (Fluidigm, San Francisco, CA). The following antibodies were used: CD45-Y89 (cat #3089005B), CD3e-Sm152 (cat #3152004B), FoxP3-Gd158 (cat #3158003A), CD4-Nd145 (cat #3145002B), CD8a-Er168 (cat #3168003B), CD11b-Nd148 (cat #3148003B), F4/80-Nd146 (cat #3146008B), CD11c-Nd142 (cat #3142003B), Ly6G-Pr141, Ly6C-Nd150, ICOS-Yb176 (cat #3176014B), and live-dead-Pt-195. Stained cells were run on the Helios Mass Cytometer at the University of Colorado Denver Cancer Center Flow Cytometry Core. Data were analyzed using Kaluza or FlowJo Analysis software.

Immunoblotting

For immunoblotting, protein cell lysates were prepared and ran onto 10% SDS-PAGE gels followed by transfer to PVDF membranes and western blotting. Blots were probed overnight at 4° C. with primary antibodies. Anti-p-AKT (1:1000, cat #4058), anti-AKT (1:1000, cat #9272), anti-Bcl-XL (1:1000, cat #2764), anti-cleaved caspase-3 (1:1000, cat #9579) and anti-β-actin antibodies (1:5000, cat #12262) were purchased from Cell Signaling Technology (Danvers, Mass., USA). Anti-EphB4 (clone m265) was provided by Vasgene Therapeutics Inc. (Los Angeles, CA, USA) or purchased from R&D Systems (cat #AF446). Horseradish peroxidase (HRP)-conjugated secondary antibodies were obtained from Sigma (St. Louis, MO, USA). For p-EphB4 analysis, CD4+ T cells were isolated from mouse spleno-cytes using EasySep CD4+ T cell isolation kit (Stemcell Technologies) and seeded in a 6-well plate followed by treatment with pre-clustered control Fc, ephrin-B2-Fc (20 μg/ml), or PEG-TNYL-RAW-Fc (4.5 μg/ml) with ephrin-B2-Fc (2.5 μg/ml) at 37° C. for 72 hours. Pre-clustering was performed as described above. Lysates were collected and run on a 10% SDS-PAGE as described above. Membranes were probed with p-EphB4 (1:1000, cat #PA5-64792, ThermoFisher) and anti-8-actin antibodies.

Immunofluorescence Staining

Immunofluorescence (IF) staining was performed on paraffin-embedded sections fixed in 4% buffered formalin. Tumor tissue sectioned at 4 μm was deparaffinized and hydrated, and antigen epitope retrieval was performed by incubating the slides in antigen retrieval buffer (Vector Laboratories) for 10-15 minutes. Sections were incubated with primary antibodies overnight at 4° C. The following antibodies were used: CD107b (1:100, cat #550292, BD Pharmingen), CD163 (1:100, cat #orb13303, Biorbyt), Gpr18 (1:100, cat #NBP2-24918SS, Novus Biologicals), F4/80 (1:50, cat #NB600-404SS, Novus Biologicals), Foxp3 (1:1000, cat #ab20034, Abcam), F4/80 (1:100, cat #70076, Cell Signaling), and Pan-Keratin (1:100, cat #4545, Cell Signaling). Primary antibody incubation was followed by treatment with AlexaFlour-tagged IgG secondary antibody (1:400 dilution, Life Technologies). Nuclei were counter-stained with 6-diamidino-2-phenylindole dihydrochloride hydrate (DAPI). Images were captured with a 20× objective using a Nikon fluorescence or Olympus confocal micro-scope. Each experiment was replicated at least twice. Analysis was performed on 6-8 random fields for each of the experimental and control groups.

ELISA

Plasma samples collected from TNYL-RAW-Fc and pcDNA3 control mice were isolated and subjected to ELISA to measure the levels of TNYL-RAW-Fc as described earlier. Briefly, 96-well plates were coated with anti-human IgG-Fc capture antibody (10 μg/ml) and incubated overnight at 4° C. The wells were blocked with BSA (5 mg/ml in PBS) for 1 hat room temperature. Plasma samples diluted at 1:100 or recombinant human Fc (R&D Systems) as a standard were added to the pre-coated wells. The goat anti-human Fc-HRP (1:700 dilution, Southern Biotech) was added for 1 hour at room temperature and following washes, TMB substrate was added, and absorbance was measured at 450 nm. To detect TGF-β1 levels, plasma samples or cell culture supernatants/conditioned media were analyzed using a TGF-β ELISA kit (R&D systems) according to the manu-facturer's instructions.

U-Plex Cytokine Array

Retro-orbital blood collection was performed on mice 11-18 days after hydrodynamic injection of TNYL-RAW-Fc plasmid (immunocompetent mouse model) or 96 hours after RT (nude mouse model). Plasma was isolated and subjected to U-plex array (Meso Scale Diagnostics, Rockville, MD) according to the manufacturer's instructions.

CIBERSORT, TCGA, and mRNA Expression Analysis

Gene expression data were obtained from the HNSCC cohort in the TOGA database (n=530). The TOGA provides level 3 RNA-seq data which has been aligned to the refer-ence genome and quantified at the gene transcripts level using RNA-Seq by Expectation Maximization (RSEM). The CIBERSORT analysis was performed as described earlier. Only cases with a p-value <0.05, which indicates a reliable estimation of immune cell infiltration, were used for further survival analysis. A cutoff value for M1:M2 of 0.5 was assigned for survival analysis. EphB4 and Ephrin-B2 expression was analyzed by using the R2 platform.

Irradiation

Irradiation was performed either using the RS-2000 irra-diator (Rad Source Technologies, GA) at 160 kVp, 10 mA or the PXi-225Cx image-guided irradiator (PXi inc, KC) at 225 kVp, 13 mA with 0.3 mm Cu filter. Mice were posi-tioned in the prone orientation and a CT scan was acquired. Treatment planning and radiation dose delivery were per-formed as described. Radiation was delivered at a dose rate of 5.6 Gy/min.

Statistical Analysis

Statistical analysis was performed using GraphPad Prism software. All the experiments were performed in duplicate or triplicate and repeated 2-3 times. Statistical analyses of differences between two groups were performed using Student's t-test or one-way ANOVA. The Dunnett's post-hoc test was used for further validation after ANOVA where multiple experimental groups were compared to the control group. A p-value of <0.05 was considered significant.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each subject publication was specifically and subjectly indicated to be incorporated by reference in its entirety for any and all purposes. The invention illustratively described herein suitably may be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

SEQUENCE LISTINGS

The amino acid sequences listed in the accompanying sequence listing are shown using standard three letter code for amino acids, as defined in 37 C.F.R. 1.822.

SEQ ID NO: 1 is the amino acid sequence of
human ephrin type-B receptor precursor
(NP_004435.3). Amino acid residues 1-15
encode a signal sequence.
(SEQ ID NO: 1)
MELRVLLCWASLAAALEETLLNTKLETADLKWVTFPQVDGQWEELSGLDE

EQHSVRTYEVCDVQRAPGQAHWLRTGWVPRRGAVHVYATLRFTMLECLSL

-continued

PRAGRSCKETFTVFYYESDADTATALTPAWMENPYIKVDTVAAEHLTRKR

PGAEATGKVNVKTLRLGPLSKAGFYLAFQDQGACMALLSLHLFYKKCAQL

TVNLTRFPETVPRELVVPVAGSCVVDAVPAPGPSPSLYCREDGQWAEQPV

TGCSCAPGFEAAEGNTKCRACAQGTFKPLSGEGSCQPCPANSHSNTIGSA

VCQCRVGYFRARTDPRGAPCTTPPSAPRSVVSRLNGSSLHLEWSAPLESG

GREDLTYALRCRECRPGGSCAPCGGDLTFDPGPRDLVEPWVVVRGLRPDF

TYTFEVTALNGVSSLATGPVPFEPVNVTTDREVPPAVSDIRVTRSSPSSL

SLAWAVPRAPSGAVLDYEVKYHEKGAEGPSSVRFLKTSENRAELRGLKRG

ASYLVQVRARSEAGYGPFGQEHHSQTQLDESEGWREQLALIAGTAVVGVV

LVLVVIVVAVLCLRKQSNGREAEYSDKHGQYLIGHGTKVYIDPFTYEDPN

EAVREFAKEIDVSYVKIEEVIGAGEFGEVCRGRLKAPGKKESCVAIKTLK

GGYTERQRREFLSEASIMGQFEHPNIIRLEGVVINSMPVMILTEFMENGA

LDSFLRLNDGQFTVIQLVGMLRGIASGMRYLAEMSYVHRDLAARNILVNS

NLVCKVSDFGLSRFLEENSSDPTYTSSLGGKIP1RWTAPEAIAFRKFTSA

SDAWSYGIVMWEVMSFGERPYWDMSNQDVINAIEQDYRLPPPPDCPTSLH

QLMLDCWQKDRNARPRFPQVVSALDKMIRNPASLKIVARENGGASHPLLD

QRQPHYSAFGSVGEWLRAIKMGRYEESFAAAGFGSFELVSQISAEDLLRI

GVTLAGHQKKILASVQHMKSQAKPGTPGGTGGPAPQY

SEQ ID NO: 2 is the amino acid sequence of
human serum albumin preproprotein
(NP_000468.1). Amino acid residues 25-609
encode the mature peptide.
(SEQ ID NO: 2)
MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQRLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVESKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKC

CTESLVNRRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL

What is claimed is:

1. A method for treating a subject diagnosed with urothelial cancer, comprising the administration of a soluble Ephrin type B receptor 4-Human Serum Albumin (sEphB4-HSA) polypeptide agent that inhibits EphB4 or EphrinB2 mediated functions, in combination with an antagonistic Programmed Cell Death Protein 1 (PD-1) antibody, as a first-line therapy according to a regimen determined to achieve improved objective response rates and progression free survival as compared to a subject administered with an antagonistic PD-1 antibody, wherein the sEphB4-HSA polypeptide agent is selected from the group consisting of a polypeptide which comprises residues 16-537 of SEQ ID NO: 1 directly fused to residues 25-609 of SEQ ID NO: 2; and a polypeptide which comprises residues 16-326 of SEQ ID NO: 1 directly fused to residues 25-609 of SEQ ID NO: 2.

2. A method according to claim 1, wherein the cancer is refractory to treatment with platinum-based chemotherapy.

3. A method according to claim 1, wherein the cancer is refractory to treatment with radiation therapy.

4. A method according to claim 1, wherein the cancer is refractory to treatment with an immune checkpoint inhibitor.

5. The method according to claim 1, wherein the cancer tumors express PD-L1.

6. The method according to claim 1, wherein the cancer tumors express EphrinB2.

7. The method according to claim 1, wherein the cancer tumors express PD-L1 and EphrinB2.

8. The method according to claim 1, wherein the antagonistic PD-1 antibody is selected from the group consisting of nivolumab, pembrolizumab, and pidilizumab.

\* \* \* \* \*

SEQUENCE LISTING

<160> NUMBER OF SEQ ID NOS: 2

<210> SEQ ID NO 1

<211> LENGTH: 987
<212> TYPE: PRT
<213> ORGANISM: Homo sapiens

<400> SEQUENCE: 1

```
Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Asp Val Gln
        50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
            115                 120                 125

Ala Trp Met Glu Asn Pro Tyr Ile Lys Val Asp Thr Val Ala Ala Glu
        130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
            195                 200                 205

Glu Thr Val Pro Arg Glu Leu Val Val Pro Val Ala Gly Ser Cys Val
        210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
            275                 280                 285

Pro Ala Asn Ser His Ser Asn Thr Ile Gly Ser Ala Val Cys Gln Cys
        290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
            355                 360                 365

Ser Cys Ala Pro Cys Gly Gly Asp Leu Thr Phe Asp Pro Gly Pro Arg
        370                 375                 380

Asp Leu Val Glu Pro Trp Val Val Val Arg Gly Leu Arg Pro Asp Phe
```

-continued

```
385              390              395              400

Thr Tyr Thr Phe Glu Val Thr Ala Leu Asn Gly Val Ser Ser Leu Ala
            405              410              415

Thr Gly Pro Val Pro Phe Glu Pro Val Asn Val Thr Thr Asp Arg Glu
            420              425              430

Val Pro Pro Ala Val Ser Asp Ile Arg Val Thr Arg Ser Ser Pro Ser
            435              440              445

Ser Leu Ser Leu Ala Trp Ala Val Pro Arg Ala Pro Ser Gly Ala Val
    450              455              460

Leu Asp Tyr Glu Val Lys Tyr His Glu Lys Gly Ala Glu Gly Pro Ser
465              470              475              480

Ser Val Arg Phe Leu Lys Thr Ser Glu Asn Arg Ala Glu Leu Arg Gly
            485              490              495

Leu Lys Arg Gly Ala Ser Tyr Leu Val Gln Val Arg Ala Arg Ser Glu
            500              505              510

Ala Gly Tyr Gly Pro Phe Gly Gln Glu His His Ser Gln Thr Gln Leu
            515              520              525

Asp Glu Ser Glu Gly Trp Arg Glu Gln Leu Ala Leu Ile Ala Gly Thr
    530              535              540

Ala Val Val Gly Val Val Leu Val Leu Val Val Ile Val Val Ala Val
545              550              555              560

Leu Cys Leu Arg Lys Gln Ser Asn Gly Arg Glu Ala Glu Tyr Ser Asp
            565              570              575

Lys His Gly Gln Tyr Leu Ile Gly His Gly Thr Lys Val Tyr Ile Asp
            580              585              590

Pro Phe Thr Tyr Glu Asp Pro Asn Glu Ala Val Arg Glu Phe Ala Lys
            595              600              605

Glu Ile Asp Val Ser Tyr Val Lys Ile Glu Glu Val Ile Gly Ala Gly
    610              615              620

Glu Phe Gly Glu Val Cys Arg Gly Arg Leu Lys Ala Pro Gly Lys Lys
625              630              635              640

Glu Ser Cys Val Ala Ile Lys Thr Leu Lys Gly Gly Tyr Thr Glu Arg
            645              650              655

Gln Arg Arg Glu Phe Leu Ser Glu Ala Ser Ile Met Gly Gln Phe Glu
            660              665              670

His Pro Asn Ile Ile Arg Leu Glu Gly Val Val Thr Asn Ser Met Pro
    675              680              685

Val Met Ile Leu Thr Glu Phe Met Glu Asn Gly Ala Leu Asp Ser Phe
    690              695              700

Leu Arg Leu Asn Asp Gly Gln Phe Thr Val Ile Gln Leu Val Gly Met
705              710              715              720

Leu Arg Gly Ile Ala Ser Gly Met Arg Tyr Leu Ala Glu Met Ser Tyr
            725              730              735

Val His Arg Asp Leu Ala Ala Arg Asn Ile Leu Val Asn Ser Asn Leu
            740              745              750

Val Cys Lys Val Ser Asp Phe Gly Leu Ser Arg Phe Leu Glu Glu Asn
            755              760              765

Ser Ser Asp Pro Thr Tyr Thr Ser Ser Leu Gly Gly Lys Ile Pro Ile
    770              775              780

Arg Trp Thr Ala Pro Glu Ala Ile Ala Phe Arg Lys Phe Thr Ser Ala
785              790              795              800

Ser Asp Ala Trp Ser Tyr Gly Ile Val Met Trp Glu Val Met Ser Phe
            805              810              815
```

-continued

```
Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
            835                 840                 845

Leu His Gln Leu Met Leu Asp Cys Trp Gln Lys Asp Arg Asn Ala Arg
            850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
                900                 905                 910

Gly Glu Trp Leu Arg Ala Ile Lys Met Gly Arg Tyr Glu Glu Ser Phe
            915                 920                 925

Ala Ala Ala Gly Phe Gly Ser Phe Glu Leu Val Ser Gln Ile Ser Ala
            930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
                980                 985

<210> SEQ ID NO 2
<211> LENGTH: 609
<212> TYPE: PRT
<213> ORGANISM: Homo sapiens

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
```

-continued

```
                195                 200                 205
Leu Arg Asp Glu Gly Lys Ala Ser Ser Ala Lys Gln Arg Leu Lys Cys
    210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
    370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu
```